(12) United States Patent
Cook et al.

(10) Patent No.: US 12,721,657 B2
(45) Date of Patent: Sep. 1, 2026

(54) DEVICE FOR REALIGNMENT, STABILIZATION, AND PREVENTION OF PROGRESSION OF ABNORMAL SPINE CURVATURE

(71) Applicant: Gomboc, LLC, Metairie, LA (US)

(72) Inventors: Stephen D. Cook, Metairie, LA (US); Samantha L. Salkeld, Metairie, LA (US); Laura P. Patron, Belle Chase, LA (US); Liam P. Nolan, New Orleans, LA (US); Michael C. Harrison, Metairie, LA (US)

(73) Assignee: Gomboc, LLC, Metairie, LA (US)

(*) Notice: Subject to any disclaimer, the term of this patent is extended or adjusted under 35 U.S.C. 154(b) by 530 days.

(21) Appl. No.: 18/125,102

(22) Filed: Mar. 22, 2023

(65) Prior Publication Data

US 2023/0293205 A1 Sep. 21, 2023

Related U.S. Application Data

(62) Division of application No. 16/513,490, filed on Jul. 16, 2019, now abandoned.

(60) Provisional application No. 62/701,521, filed on Jul. 20, 2018.

(51) Int. Cl.

| | |
|---|---|
| ***A61B 17/70*** | (2006.01) |
| *A61B 17/56* | (2006.01) |
| *A61F 2/44* | (2006.01) |

(52) U.S. Cl.

CPC .... *A61B 17/7001* (2013.01); *A61B 2017/564* (2013.01); *A61F 2002/448* (2013.01); *A61F 2210/009* (2013.01); *A61F 2230/0069* (2013.01); *A61F 2230/0071* (2013.01); *A61F 2250/0006* (2013.01)

(58) Field of Classification Search

CPC ... A61B 17/7014–7017; A61B 17/7032–7034; A61B 17/7001

See application file for complete search history.

(56) References Cited

U.S. PATENT DOCUMENTS

| | | | |
|---|---|---|---|
| 4,024,588 | A | 5/1977 | Janssen et al. |
| 5,879,386 | A | 3/1999 | Jore |
| 6,599,321 | B2 | 7/2003 | Hyde, Jr. |
| 8,721,566 | B2 | 5/2014 | Connor et al. |
| 8,986,349 | B1 | 3/2015 | German et al. |

(Continued)

FOREIGN PATENT DOCUMENTS

| | | |
|---|---|---|
| WO | WO-2006089292 A2 | 8/2006 |
| WO | WO-2007084416 A2 | 7/2007 |

(Continued)

*Primary Examiner* — Eduardo C Robert
*Assistant Examiner* — Michelle C Green
(74) *Attorney, Agent, or Firm* — Grimes & Yvon LLP

(57) ABSTRACT

A magnetic screw device of a bone screw and one or more magnets that are attached to the bone screw. The bone screw may have a stem, which comprises a connector and at least one thread, and a housing assembly. The connector of the stem may be configured to articulate with the housing assembly such that the stem can rotate and angulate relative to the housing assembly. The magnetic screw device may be used to treat or stabilize spines with abnormal curvature, prevent further curvature progression, and relieve pain associated with abnormal curvature.

19 Claims, 28 Drawing Sheets

(56) References Cited

U.S. PATENT DOCUMENTS

| | | | |
|---|---|---|---|
| 9,060,813 | B1 | 6/2015 | Uribe |
| 9,579,135 | B2 | 2/2017 | Cook et al. |
| 2004/0059423 | A1 | 3/2004 | Barnes et al. |
| 2006/0074448 | A1 | 4/2006 | Harrison et al. |
| 2007/0100457 | A1 | 5/2007 | Hyde, Jr. |
| 2008/0306324 | A1 | 12/2008 | Bonutti et al. |
| 2010/0094306 | A1 | 4/2010 | Chang et al. |
| 2011/0257754 | A1 | 10/2011 | Fleischmann |
| 2014/0081334 | A1 | 3/2014 | Jackson et al. |
| 2014/0296919 | A1* | 10/2014 | Culbert ..................... A61F 2/44 606/272 |
| 2015/0297265 | A1* | 10/2015 | Arena ................ A61B 17/7016 606/258 |
| 2017/0231768 | A1 | 8/2017 | Gross |
| 2017/0265900 | A1* | 9/2017 | Lai ....................... A61B 17/705 |
| 2018/0014838 | A1* | 1/2018 | Ning .................. A61B 17/7023 |
| 2018/0117350 | A1 | 5/2018 | Compton et al. |
| 2019/0021776 | A1* | 1/2019 | Archbold ........... A61B 17/8625 |
| 2019/0053908 | A1 | 2/2019 | Cook et al. |

FOREIGN PATENT DOCUMENTS

| | | | |
|---|---|---|---|
| WO | WO-2009105104 | A1 | 8/2009 |
| WO | WO-2018005792 | A1 | 1/2018 |

* cited by examiner

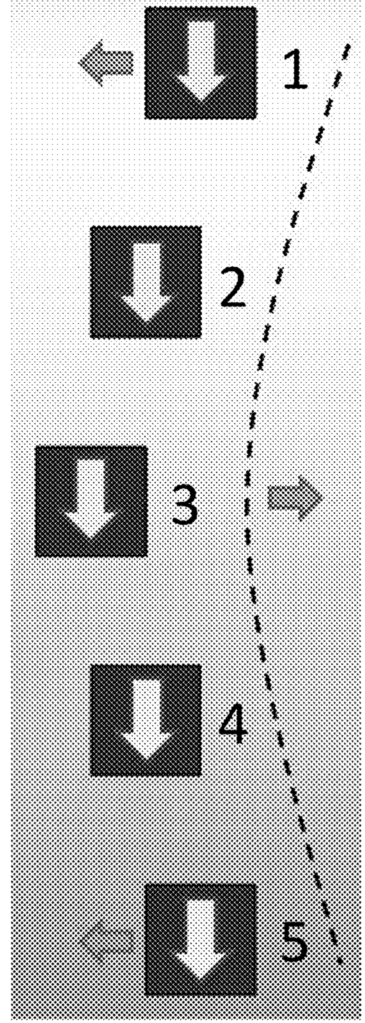
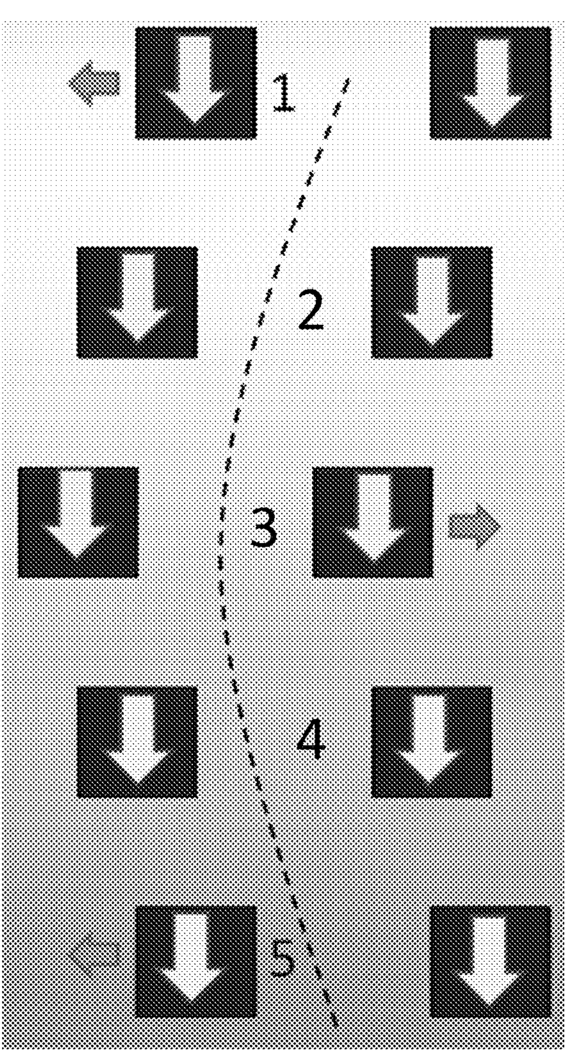
Figure 8A
Figure 8B

Vertebral Level

Vertebral Level

DEVICE FOR REALIGNMENT, STABILIZATION, AND PREVENTION OF PROGRESSION OF ABNORMAL SPINE CURVATURE

CROSS-REFERENCE TO RELATED APPLICATIONS

This application is a divisional of U.S. application Ser. No. 16/513,490 filed on Jul. 16, 2019, which claims the benefit of U.S. Provisional Application Ser. No. 62/701,521 filed on Jul. 20, 2018, the entireties of both applications of which are herein incorporated by reference.

FIELD OF INVENTION

The present invention generally relates to prosthetic devices and their use. In particular, the present invention devices containing magnets for use in treating or preventing the progression of abnormal curvatures in the spine.

BACKGROUND OF THE INVENTION

Scoliosis is a condition of the spine that primarily affects young adolescents—typically between the ages of 10 and full growth—and more often females than males. The condition causes the spine to curve sideways, such that from an anterior or posterior view the spine resembles a letter "C" or "S" rather than a straight line. An example of a C-type curvature is provided in FIG. 1, which shows the vertebral bodies 5, 5', and 5" of three adjacent vertebrae 1, 1', and 1", respectively, not in alignment. The curvature associated with scoliosis most often occurs in the upper and middle back. Scoliosis screening is a routine and standard procedure in all young adolescents, because it requires only an external examination while the patient is in the bent position.

There are several types of scoliosis, including congenital, which develops before birth; and neuromuscular, such as muscular dystrophy or cerebral palsy. However, the most common is idiopathic, in which the cause of the curve is unknown. Idiopathic curves vary in size and mild curves are more common than larger curves. But if a child is still growing, a scoliosis curve can worsen rapidly during a growth spurt.

In general, curves less than 25 degrees (determined using the Cobb method of measuring the degree of scoliosis) are typically monitored every six to twelve months by radiographs for progression of the deformity. Curves greater than 25 degrees are considered serious enough to require treatment. Curves 25 to 45 degrees in a growing child are most often treated using braces in an attempt to stabilize the spine and prevent further curve progression that would require surgery. However, bracing does not straighten the spine, and its efficacy in stabilizing the spine varies; in the United States, it is successful in preventing curve progression in as many as 30,000 cases each year, but unsuccessful in about 40,000 cases, in which surgery is required.

Curves greater than 45 degrees or those continuing to progress with bracing may undergo fusion surgery, which involves the attachment of metal rods and screws, wires, and/or hooks to the spine using bone graft material in order to straighten the spine and fuse the vertebrae together. However, fusion surgery can require a long recovery time and has a risk of neurologic complications and infection. Surgery may also fail to reduce the pain caused by spinal curvature, and may lead to further spine degradation and curve changes.

Thus, there remains a need in the art in patients with scoliosis for an intervention that effectively realigns the spine over time, stabilizes the spine, and/or prevents further curve progression.

SUMMARY OF INVENTION

One aspect of the present invention relates to a magnetic screw device.

The magnetic screw device may comprise a bone screw and one or more magnets attached to the bone screw. The bone screw may comprise a stem that comprises a connector and at least one thread. In embodiments of the invention, the bone screw may further comprise a housing assembly. In some embodiments, the connector of the stem may be configured to articulate with the housing assembly such that the stem can rotate and angulate relative to the housing assembly. In some embodiments, the one or more magnets may be attached to the housing assembly of the bone screw.

In some embodiments, the housing assembly may comprise an outer shell and an inner shell, and the inner shell is fit within the outer shell. The inner shell may comprise a hollow cylinder. In certain embodiments, the connector of the stem may be configured to articulate with the inner shell of the housing assembly.

In some embodiments, the connector may be generally spherical and, in certain embodiments, the inner shell or a portion thereof of the housing assembly may comprise a curved surface in order to articulate with the connector.

In some embodiments, the bone screw may further comprise a locking mechanism that can lock the stem at a set rotation and angulation relative to the housing assembly. In certain embodiments, the locking mechanism may comprise a set screw.

In some embodiments, the one or more magnets may be attached to the housing assembly or to the locking mechanism. In some embodiments, the one or more magnets may be enclosed in a casing. The one or more magnets may comprise a material that is iron-based, nickel-based, cobalt-based, or an alloy of rare-earth metals. In certain embodiments, the one or more magnets comprise an alloy of neodymium, iron, and boron.

Other aspects of the present invention relate to methods of use of the magnetic screw device. Embodiments of the invention are directed to a method of treating a spine with an abnormal curvature in a subject in need thereof; a method of stabilizing a spine with an abnormal curvature in a subject in need thereof; a method of correcting an abnormal curvature in a spine over time; a method of preventing curve progression of a spine with an abnormal curvature in a subject in need thereof; a method of reducing the risk of curve progression of a spine with an abnormal curvature in a subject in need thereof; a method of aligning vertebrae in a spine with an abnormal curvature in a subject in need thereof; or a method of aiding the realignment of a spine with an abnormal curvature in a subject in need thereof.

In some embodiments, the methods may comprise implanting one or more magnetic screw devices into two or more vertebrae at the curvature. The magnetic screw device may be implanted into one of the pedicles of each of the two or more vertebrae, or it may be implanted into both pedicles of each of the two or more vertebrae.

In some embodiments, upon implantation, the magnet(s) of each implanted magnetic screw device may be oriented such that the poles of the magnet(s) of the implanted magnetic screw devices are aligned.

In some embodiments, the methods may further comprise implanting one or more magnetic screw devices into two or more vertebrae that are adjacent to the vertebrae at the curvature.

In some embodiments, the subject may wear an external brace that comprises one or more magnets, in which the one or more magnets in the external brace may be oriented to have the same magnetic pole alignment as the one or more magnets of the implanted magnetic screw devices.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications, and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the magnetic screw devices of the present invention and methods of their use.

Figure 4A:
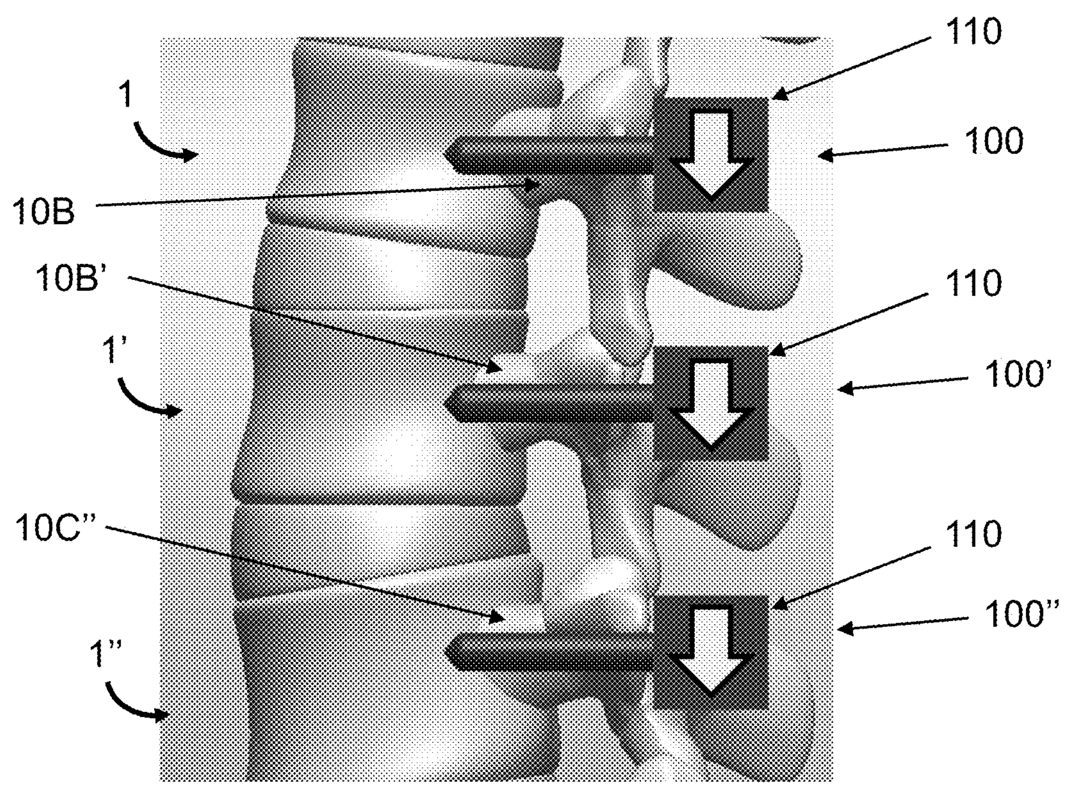
Figure 4B:
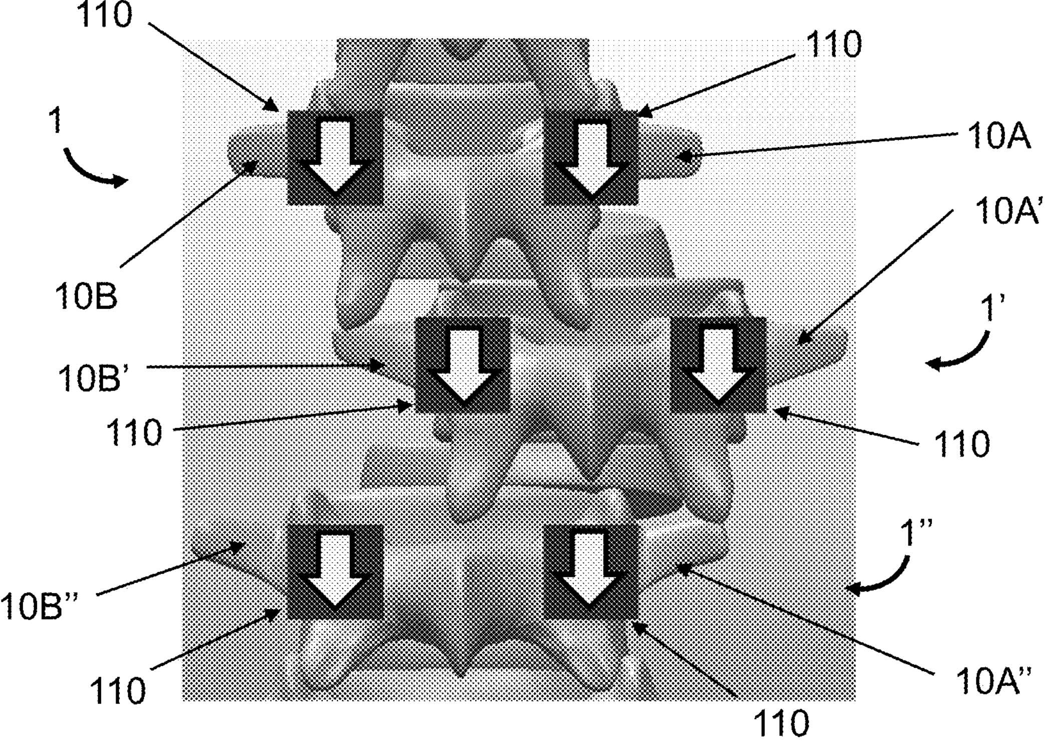

FIGS. 4A and 4B are different views of magnetic screw devices implanted into the vertebrae of an abnormal curvature in the human spine, according to embodiments of the present invention. FIG. 4A is lateral view, and FIG. 4B is a posterior view. The vertical arrows depict the direction of the poles of the magnets of the magnetic screw devices.

Figure 5:
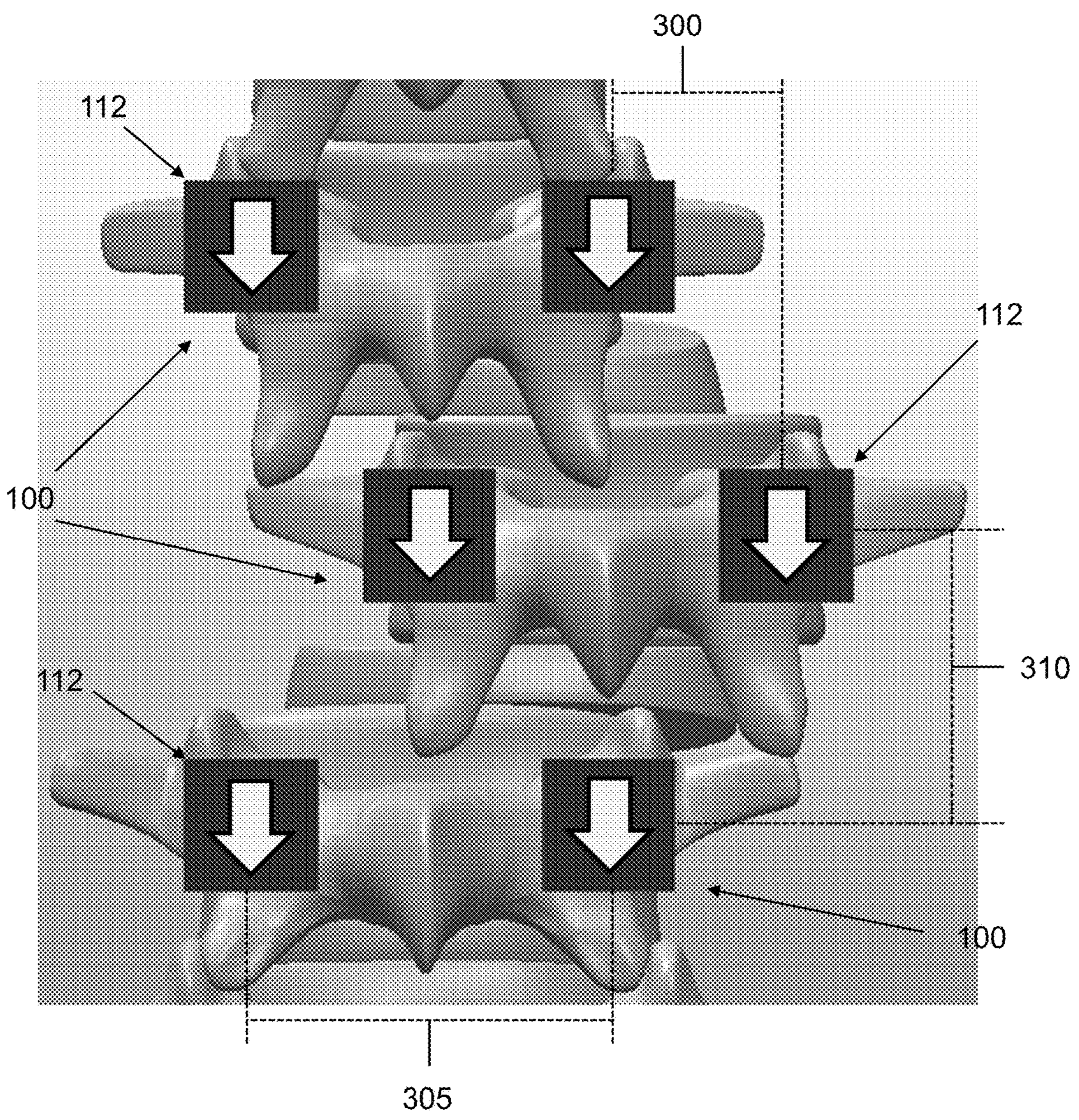

FIG. 5 is a posterior view of magnetic screw devices implanted into the vertebrae of an abnormal curvature in the human spine, according to embodiments of the present invention, marked to identify offset distance, vertical distance, and horizontal distance. The vertical arrows depict the direction of the poles of the magnets of the magnetic screw devices.

Figure 6A:
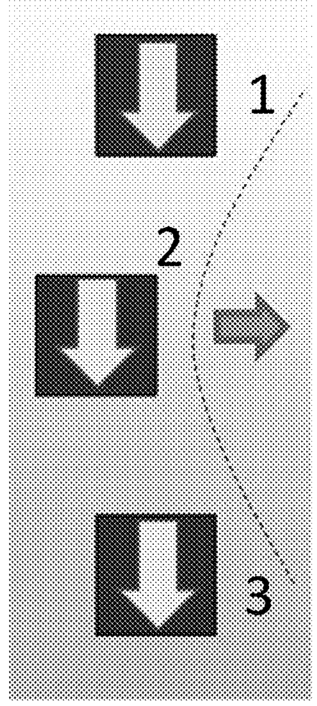
Figure 6B:
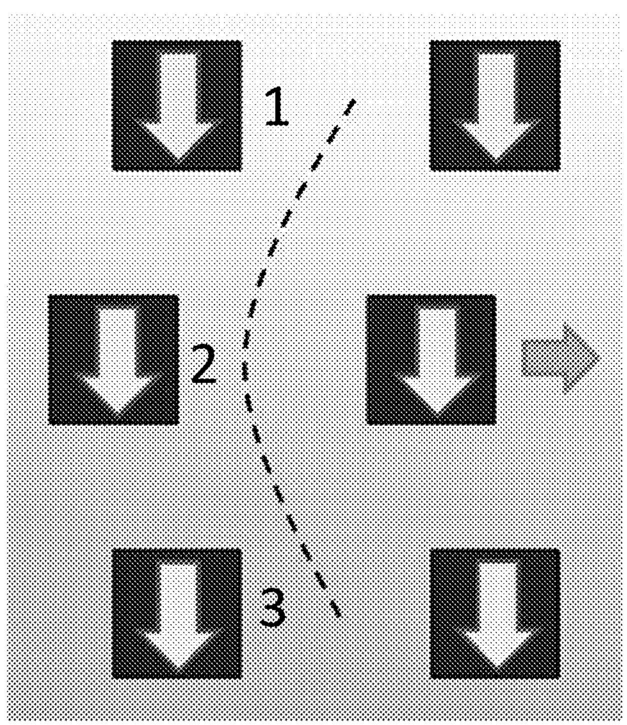

FIGS. 6A and 6B are configurations of implanted magnetic screw devices relative to a 3-vertebrae-level abnormal C-type spinal curvature, according to embodiments of the present invention, and as set forth in Example 1. The magnetic screw devices are positioned in the area of the abnormal C-type curvature and at various offset distances. FIG. 6A is a configuration of the magnetic screw devices implanted into one pedicle of each vertebra, and FIG. 6B is a configuration of the magnetic screw devices implanted into both pedicles of each vertebra. The vertical arrows depict the direction of the poles of the magnets of the magnetic screw devices, and the horizontal arrow depicts the direction of the centering forces on the vertebrae. The dashed line represents the mid-line axis of the spine.

Figure 7:
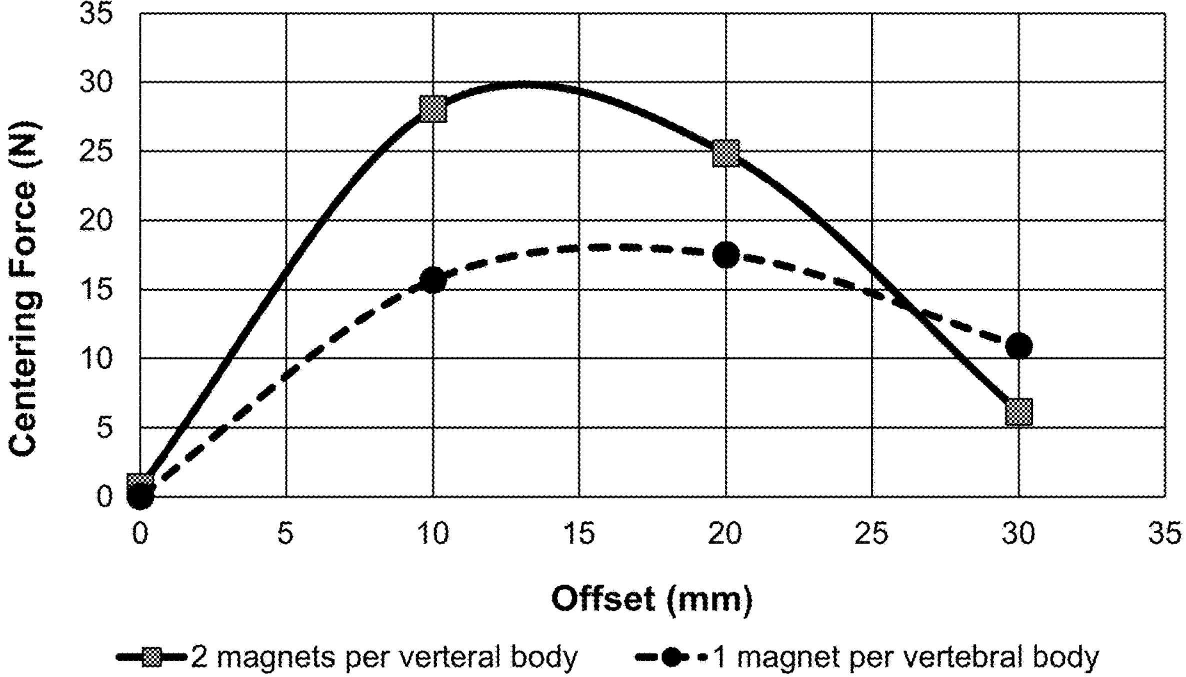

FIG. 7 is a plot of the centering forces generated by implanted magnetic screw devices that are positioned in the area of a 3-vertebrae-level abnormal C-type spinal curvature, according to embodiments of the present invention, and as set forth in Example 1. The magnetic screw devices are implanted at various offset distances, and in one or both pedicles of each vertebra, and the plot is specific to the centering forces generated by the magnetic screw devices implanted in the middle vertebrae of the 3-vertebrae-level abnormal C-type spinal curvature.

FIGS. 8A and 8B are configurations of implanted magnetic screw devices relative to a 5-vertebrae-level abnormal C-type spinal curvature, according to embodiments of the present invention, and as set forth in Example 2. The magnetic screw devices are positioned in the area of the abnormal C-type curvature and at an offset distance of 10 mm. FIG. 8A is a configuration of the magnetic screw devices implanted into one pedicle of each vertebra, and FIG. 8B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae. The dashed line represents the mid-line axis of the spine.

Figure 9A:
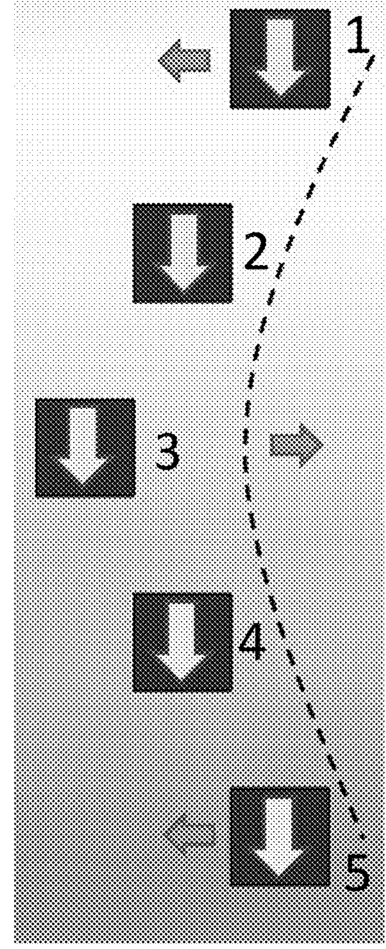
Figure 9B:
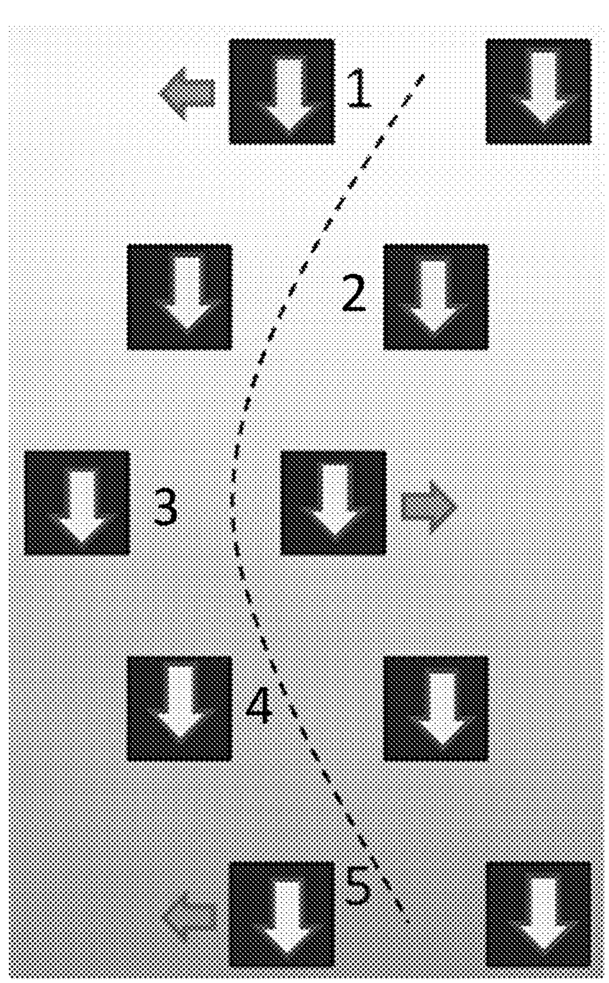

FIGS. 9A and 9B are configurations of implanted magnetic screw devices relative to a 5-vertebrae-level abnormal C-type spinal curvature, according to embodiments of the present invention, and as set forth in Example 2. The magnetic screw devices are positioned in the area of the abnormal C-type curvature and at an offset distance of 20 mm. FIG. 9A is a configuration of the magnetic screw devices implanted into one pedicle of each vertebra, and FIG. 9B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae. The dashed line represents the mid-line axis of the spine.

Figure 10:
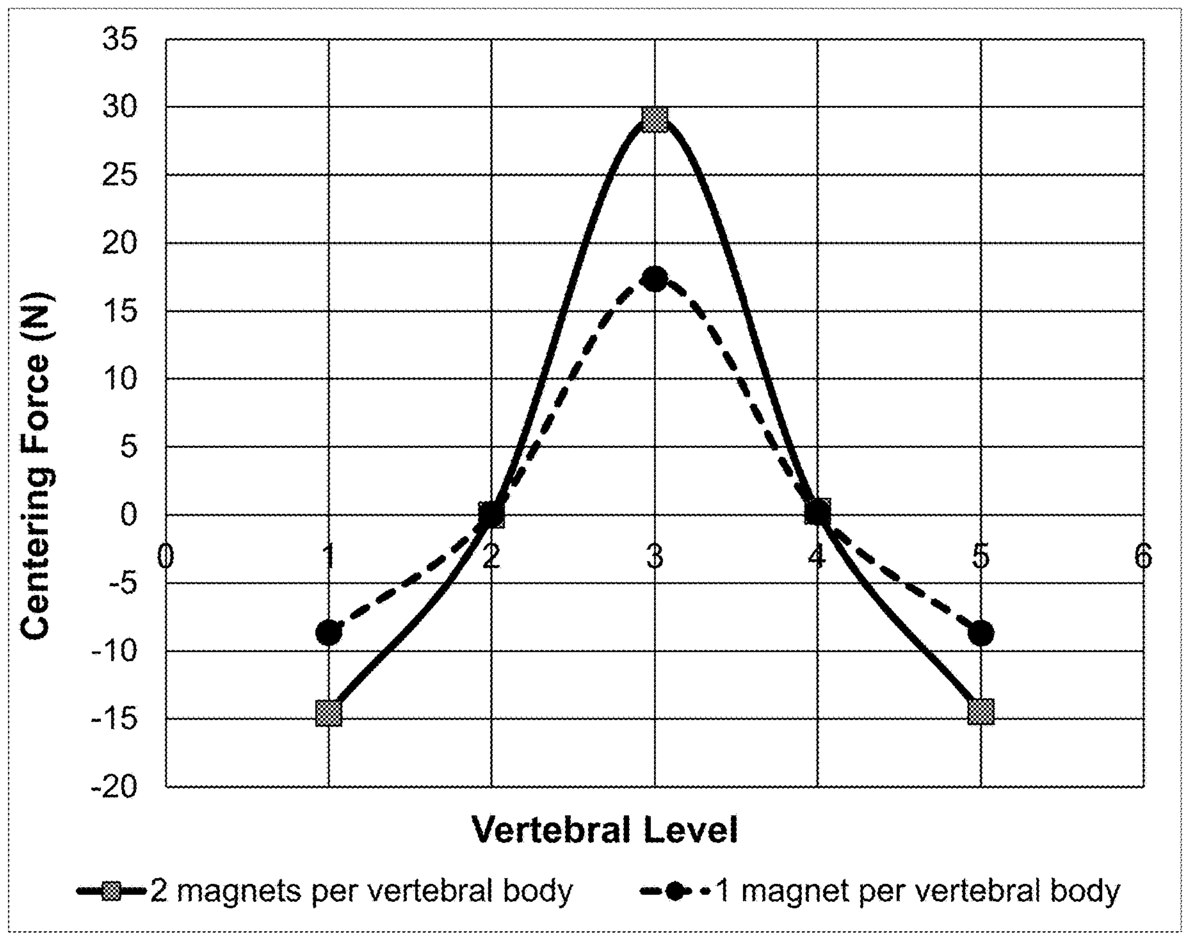

FIG. 10 is a plot of the centering forces generated at different vertebral levels by implanted magnetic screw devices that are positioned in the area of a 5-vertebrae-level abnormal C-type spinal curvature, according to embodiments of the present invention, and as set forth in Example 2. The magnetic screw devices are implanted at an offset distance of 10 mm, and in one or both pedicles of each vertebra.

Figure 11:
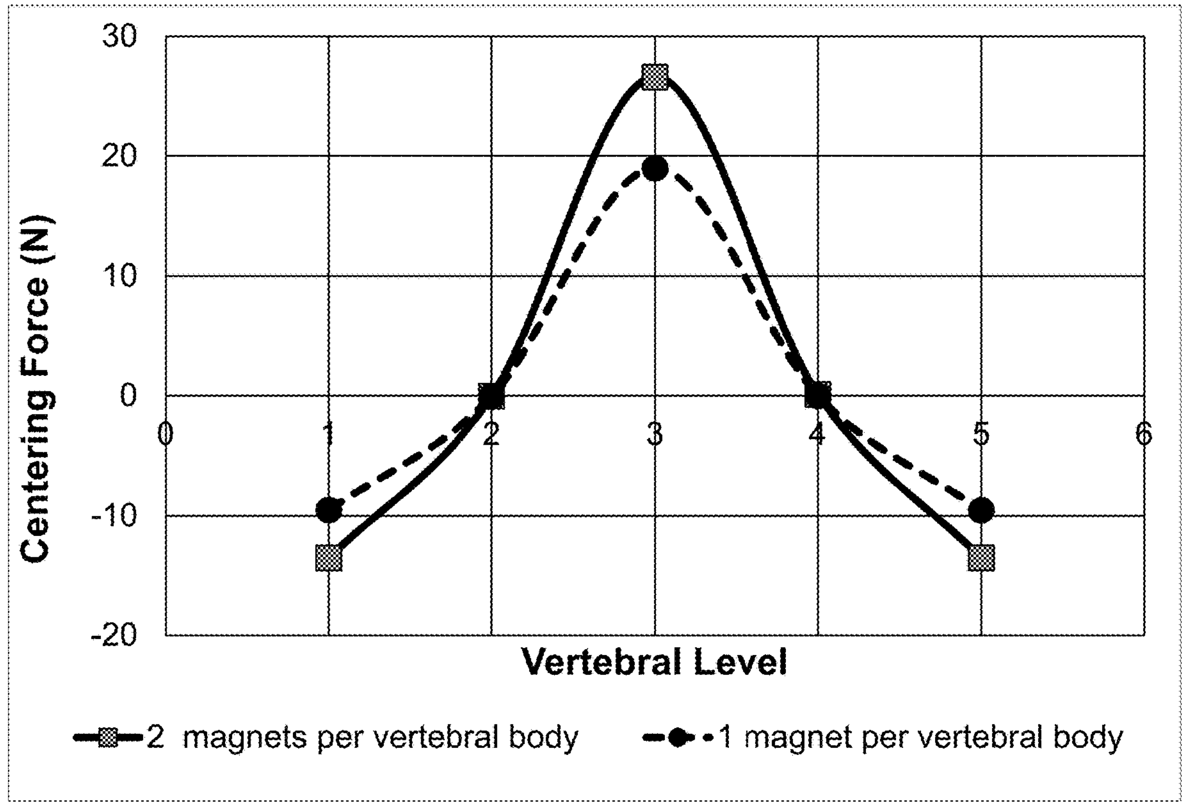

FIG. 11 is a plot of the centering forces generated at different vertebral levels by implanted magnetic screw devices that are positioned in the area of a 5-vertebrae-level abnormal C-type spinal curvature, according to embodiments of the present invention, and as set forth in Example 2. The magnetic screw devices are implanted at an offset distance of 20 mm, and in one or both pedicles of each vertebra.

Figure 12A:
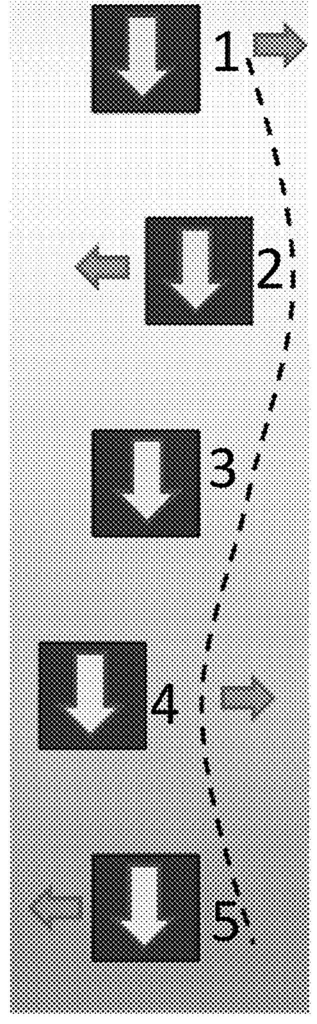
Figure 12B:
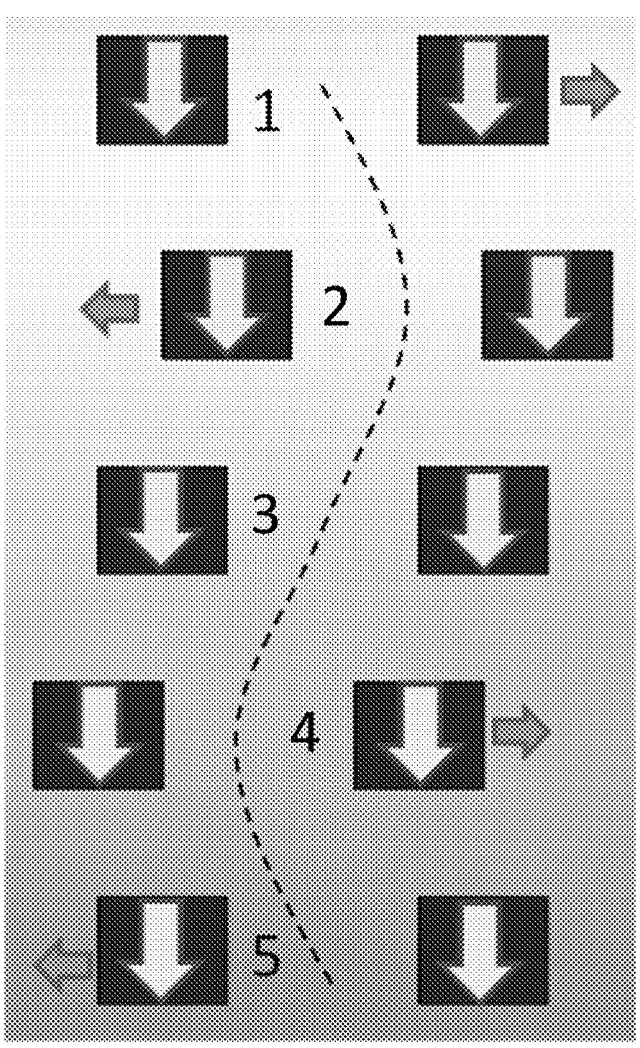

FIGS. 12A and 12B are configurations of implanted magnetic screw devices relative to a 5-vertebrae-level abnormal S-type spinal curvature, according to embodiments of the present invention, and as set forth in Example 3. The magnetic screw devices are positioned in the area of the abnormal S-type curvature and at an offset distance of 10 mm. FIG. 12A is a configuration of the magnetic screw devices implanted into one pedicle of each vertebra, and FIG. 12B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae. The dashed line represents the mid-line axis of the spine.

Figure 13A:
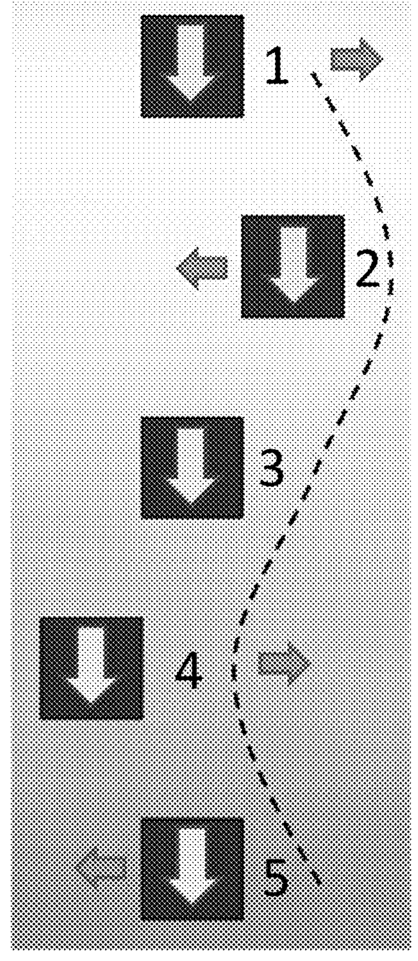
Figure 13B:
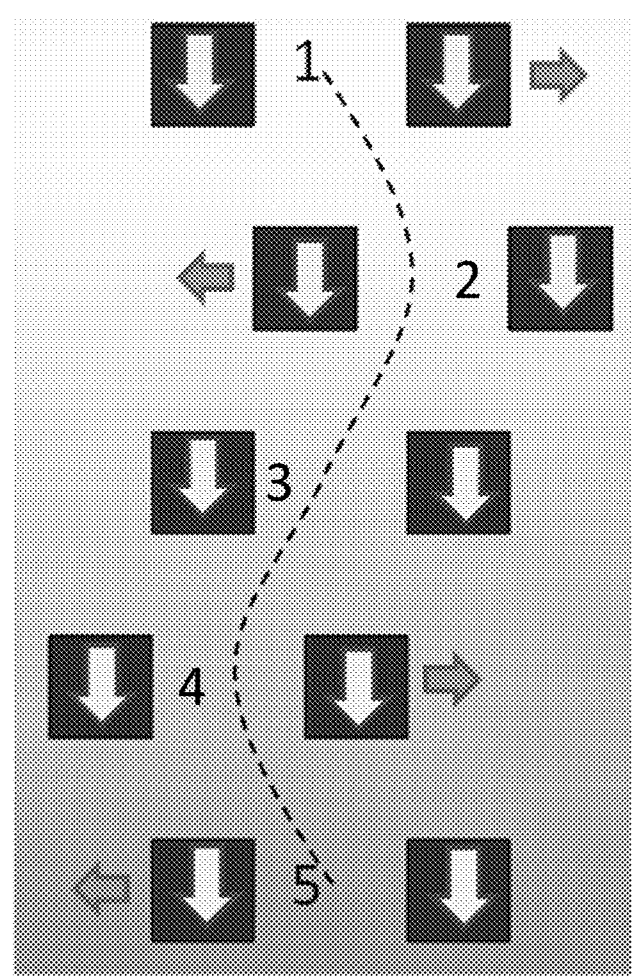

FIGS. 13A and 13B are configurations of implanted magnetic screw devices relative to a 5-vertebrae-level abnormal S-type spinal curvature, according to embodiments of the present invention, and as set forth in Example 3. The magnetic screw devices are positioned in the area of the abnormal S-type curvature and at an offset distance of 20 mm. FIG. 13A is a configuration of the magnetic screw devices implanted into one pedicle of each vertebra, and FIG. 13B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae. The dashed line represents the mid-line axis of the spine.

Figure 14:
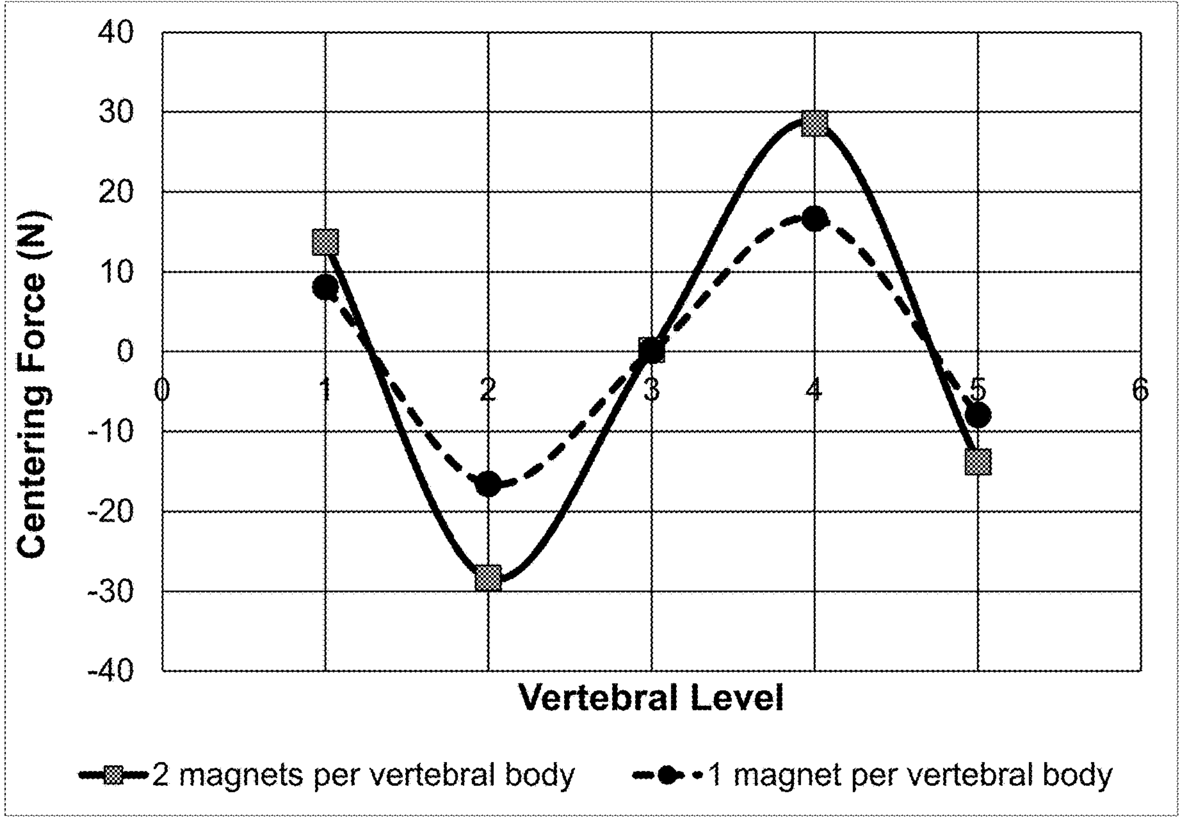

FIG. 14 is a plot of the centering forces generated at different vertebral levels by implanted magnetic screw devices that are positioned in the area of a 5-vertebrae-level abnormal S-type spinal curvature, according to embodiments of the present invention, and as set forth in Example 3. The magnetic screw devices are implanted at an offset distance of 10 mm, and in one or both pedicles of each vertebra.

Figure 15:
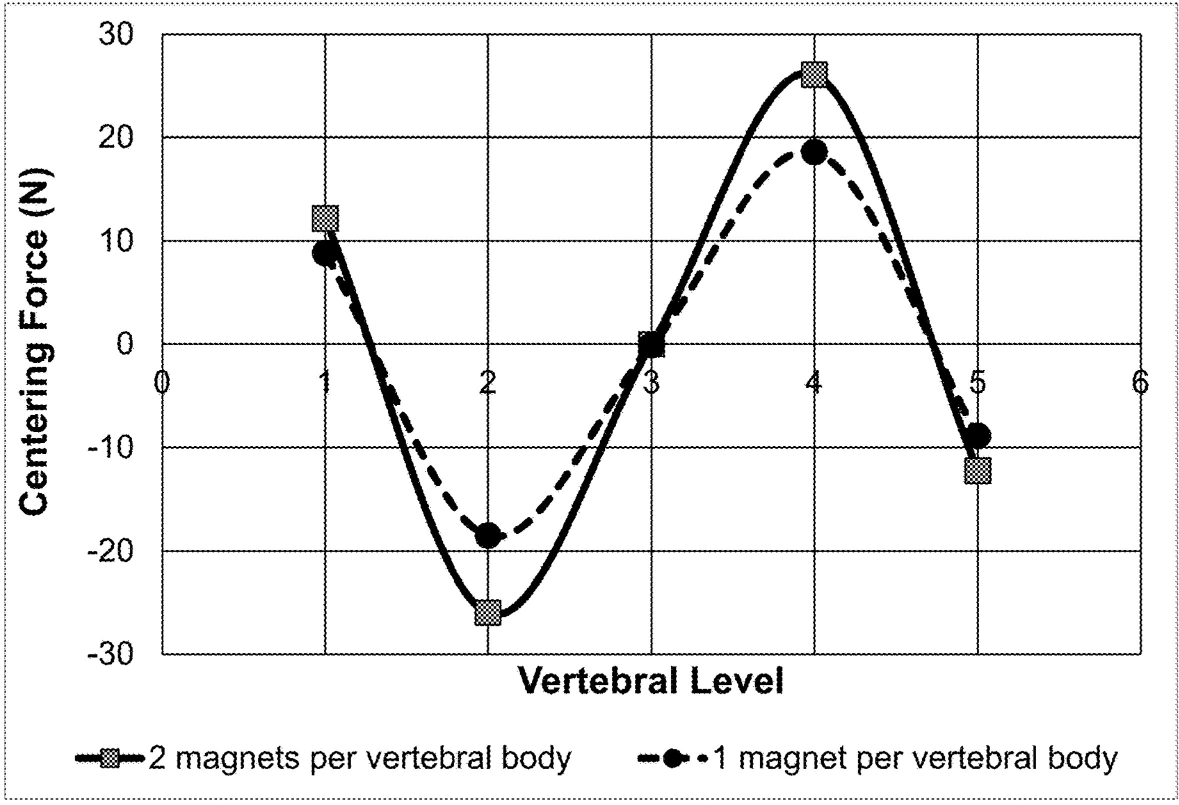

FIG. 15 is a plot of the centering forces generated at different vertebral levels by implanted magnetic screw devices that are positioned in the area of a 5-vertebrae-level abnormal S-type spinal curvature, according to embodiments of the present invention, and as set forth in Example 3. The magnetic screw devices are implanted at an offset distance of 20 mm, and in one or both pedicles of each vertebra.

Figure 16A:
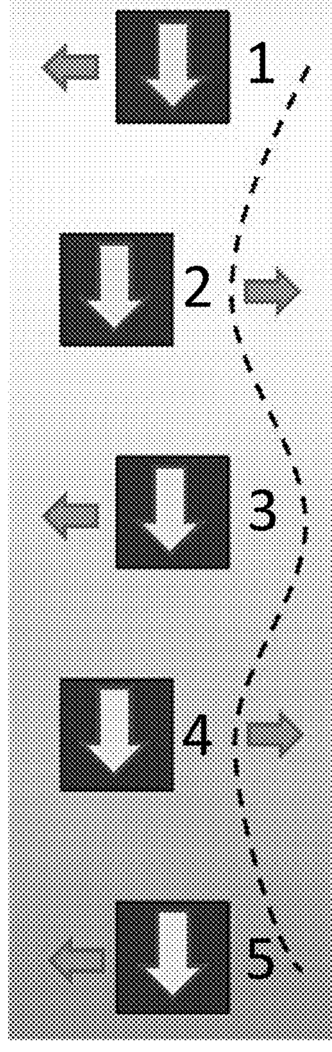
Figure 16B:
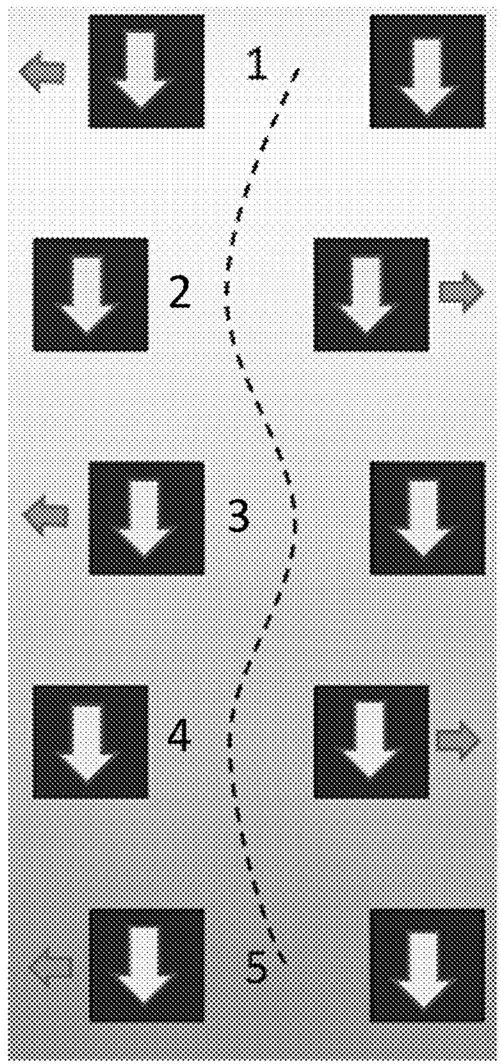

FIGS. 16A and 16B are configurations of implanted magnetic screw devices relative to a 5-vertebrae-level abnormal double S-type spinal curvature, according to embodiments of the present invention, and as set forth in Example 4. The magnetic screw devices are positioned in the area of the abnormal double S-type curvature and at an offset distance of 10 mm. FIG. 16A is a configuration of the magnetic screw devices implanted into one pedicle of each vertebra, and FIG. 16B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae. The dashed line represents the mid-line axis of the spine.

Figure 17A:
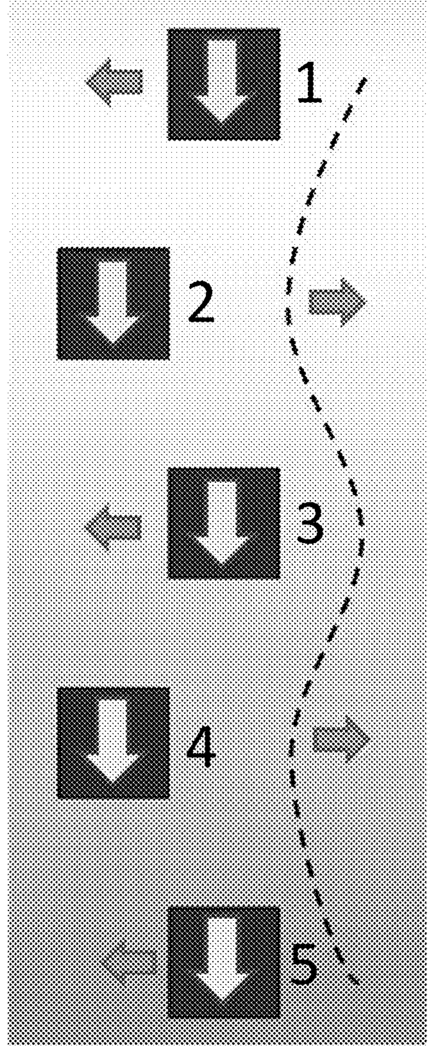
Figure 17B:
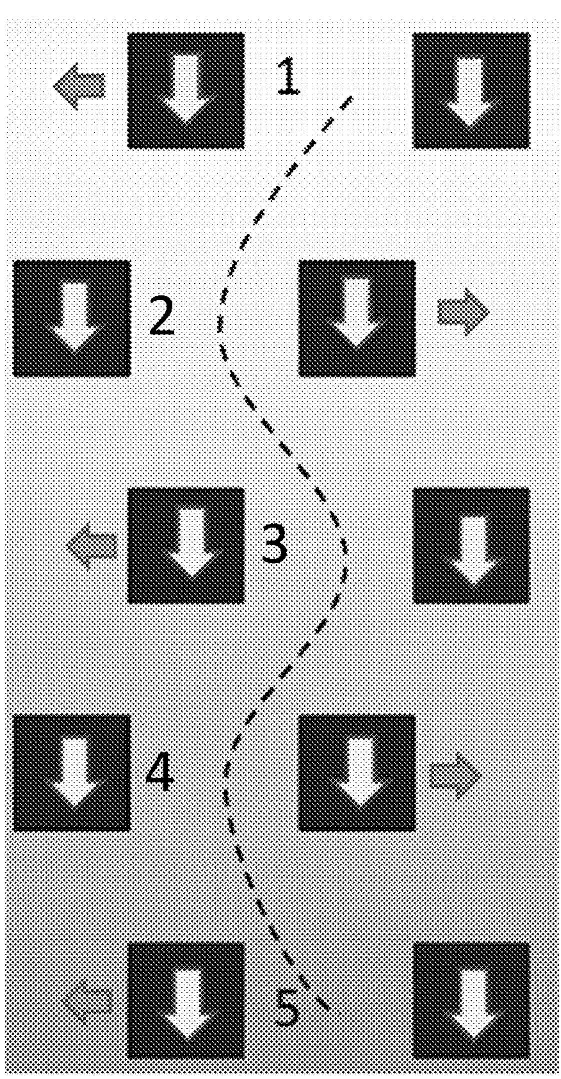

FIGS. 17A and 17B are configurations of implanted magnetic screw devices relative to a 5-vertebrae-level abnormal double S-type spinal curvature, according to embodiments of the present invention, and as set forth in Example 4. The magnetic screw devices are positioned in the area of the abnormal double S-type curvature and at an offset distance of 20 mm. FIG. 17A is a configuration of the magnetic screw devices implanted into one pedicle of each vertebra, and FIG. 17B is a configuration of the magnetic screw devices implanted into both pedicles of each vertebra. The vertical arrows depict the direction of the poles of the magnets of the magnetic screw devices, and the horizontal arrows depict the direction of the centering forces on the vertebrae.

Figure 18:
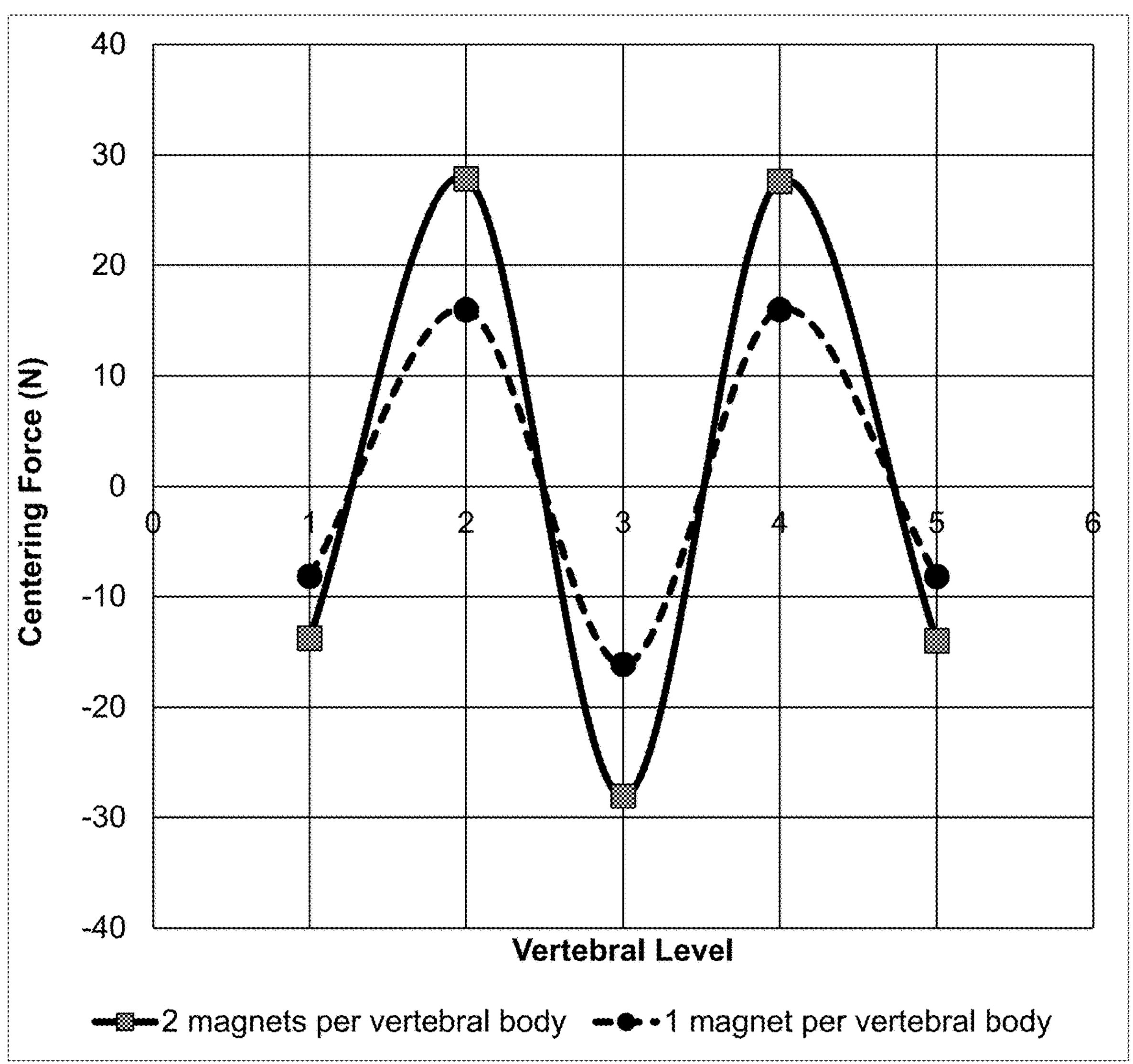

FIG. 18 is a plot of the centering forces generated at different vertebral levels by implanted magnetic screw devices that are positioned in the area of a 5-vertebrae-level abnormal double S-type spinal curvature, according to embodiments of the present invention, and as set forth in Example 4. The magnetic screw devices are implanted at an offset distance of 10 mm, and in one or both pedicles of each vertebra.

Figure 19:
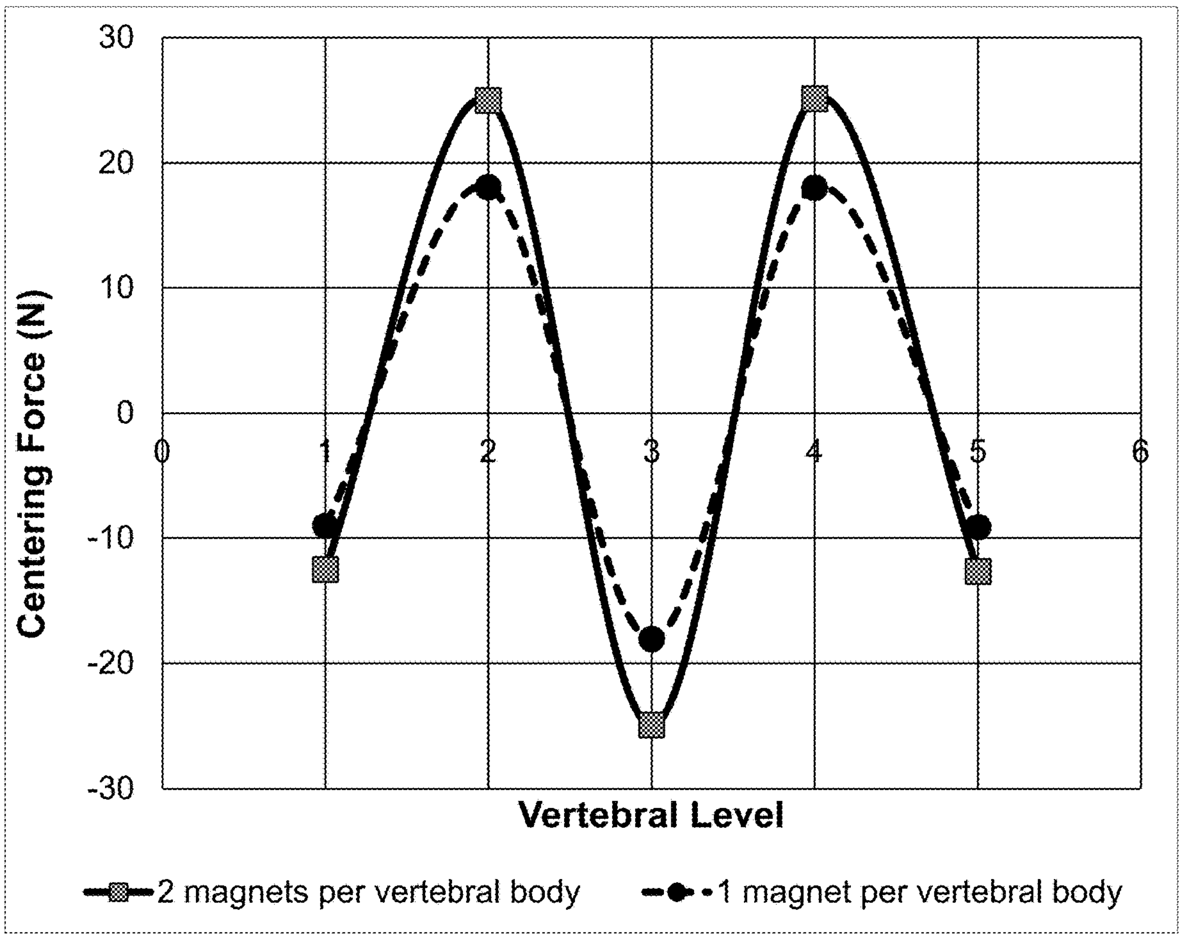

FIG. 19 is a plot of the centering forces generated at different vertebral levels by implanted magnetic screw devices that are positioned in the area of a 5-vertebrae-level abnormal double S-type spinal curvature, according to embodiments of the present invention, and as set forth in Example 4. The magnetic screw devices are implanted at an offset distance of 20 mm, and in one or both pedicles of each vertebra.

Figure 20A:
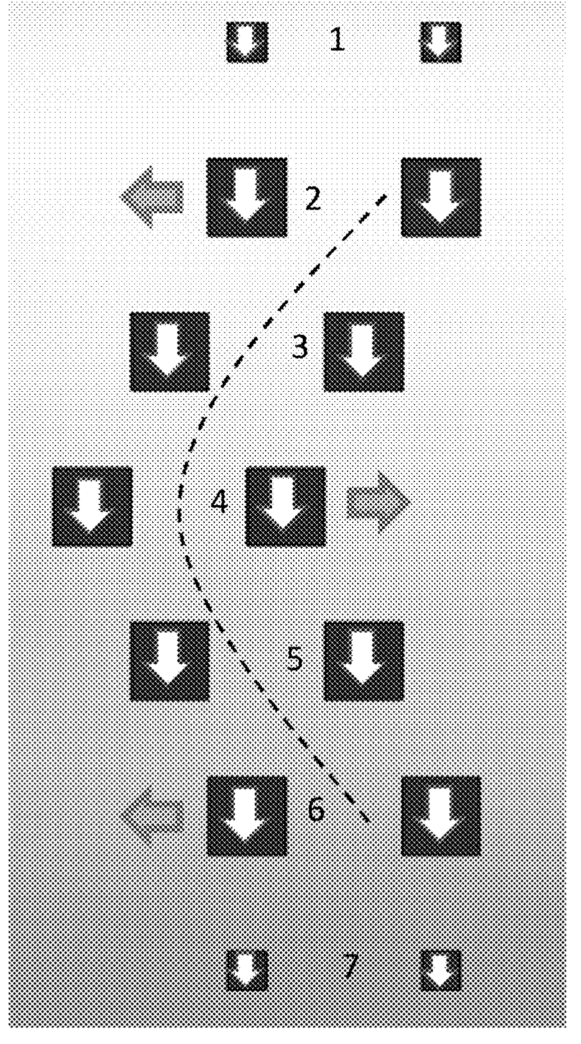
Figure 20B:
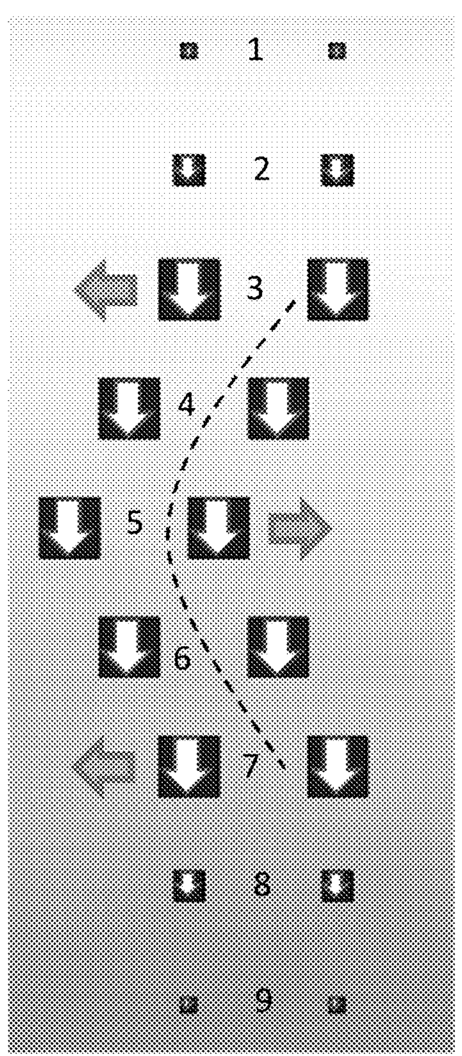

FIGS. 20A and 20B are configurations of implanted magnetic screw devices relative to 5-vertebrae-level abnormal C-type spinal curvatures, according to embodiments of the present invention, and as set forth in Example 5. The magnetic screw devices are positioned in the area of the abnormal C-type curvature, as well as in one or more one vertebra levels superior and inferior to the area of the abnormal C-type curvature, and at an offset distance of 20 mm. FIG. 20A is a configuration of implanted magnetic screw devices in vertebrae in the area of the abnormal C-type curvature, in one vertebra immediately superior to the area of the abnormal C-type curvature, and in one vertebra immediately inferior to the area of the abnormal C-type curvature. FIG. 20B is a configuration of implanted magnetic screw devices in vertebrae in the area of the abnormal C-type curvature, in two vertebrae immediately superior to the area of the abnormal C-type curvature, and in two vertebrae immediately inferior to the area of the abnormal C-type curvature. For each figure, the magnetic screw devices are implanted into both pedicles of each vertebra. The vertical arrows depict the direction of the poles of the magnets of the magnetic screw devices, and the horizontal arrows depict the direction of the centering forces on the vertebrae.

Figure 21:
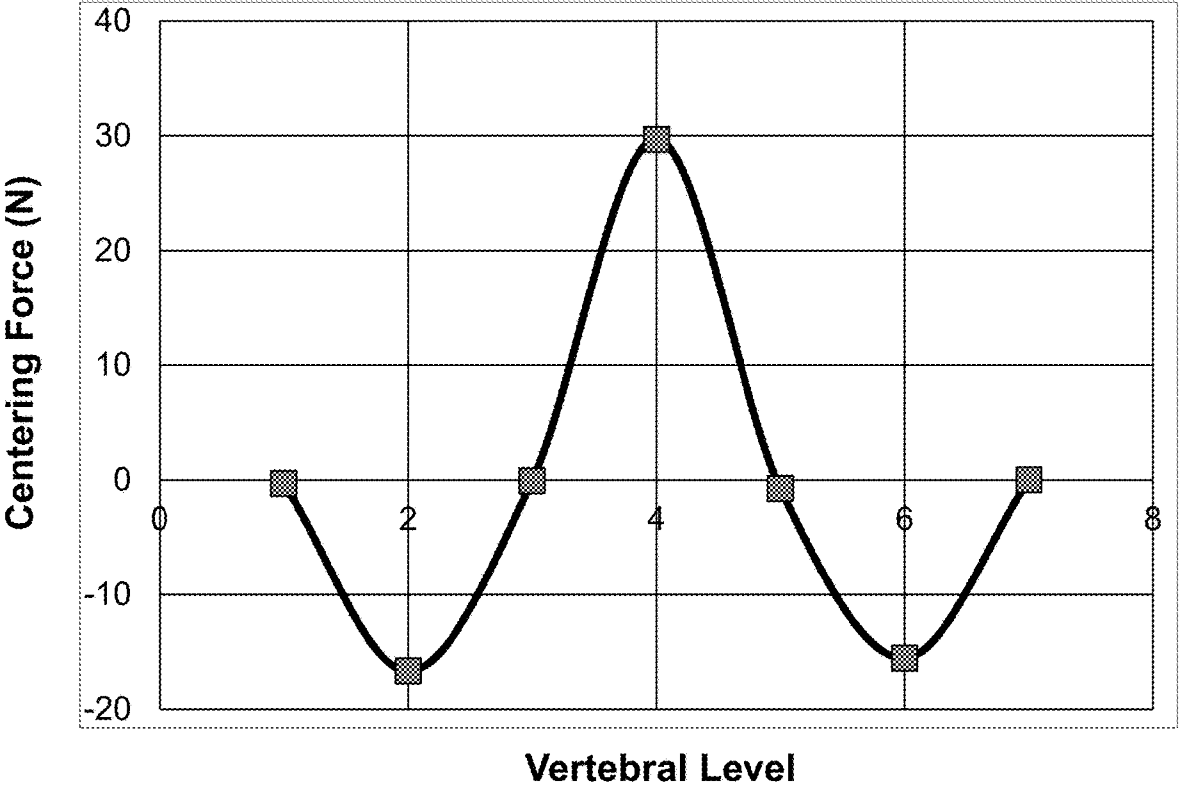

FIG. 21 is a plot of the centering forces generated at different vertebral levels by implanted magnetic screw devices that are positioned in the area of a 5-vertebrae-level abnormal C-type spinal curvature, one vertebra level immediately superior to the area of the curvature, and one vertebra level immediately inferior to the area of the curvature, according to embodiments of the present invention, and as set forth in Example 5. The magnetic screw devices are implanted at an offset distance of 20 mm, and in both pedicles of each vertebra.

Figure 22:
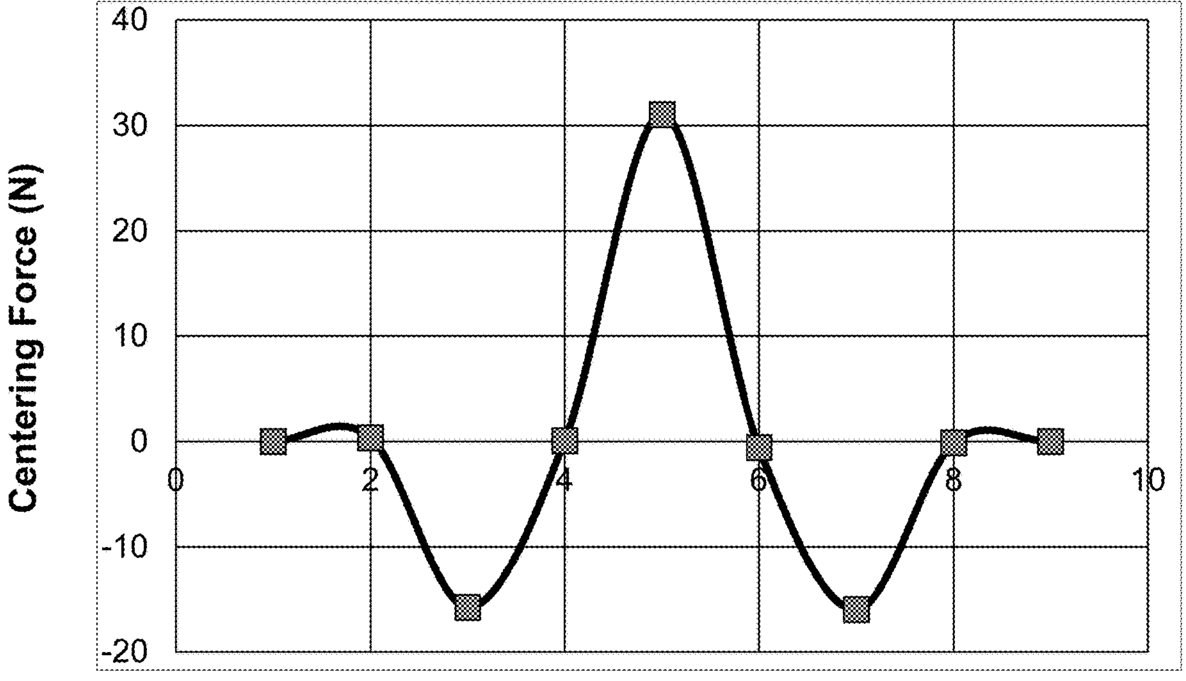

FIG. 22 is a plot of the centering forces generated at different vertebral levels by implanted magnetic screw devices that are positioned in the area of a 5-vertebrae-level abnormal C-type spinal curvature, two vertebrae levels immediately superior to the area of the curvature, and two vertebrae levels immediately inferior to the area of the curvature, according to embodiments of the present invention, and as set forth in Example 5. The magnetic screw devices are implanted at an offset distance of 20 mm, and in both pedicles of each vertebra.

Figure 23A:
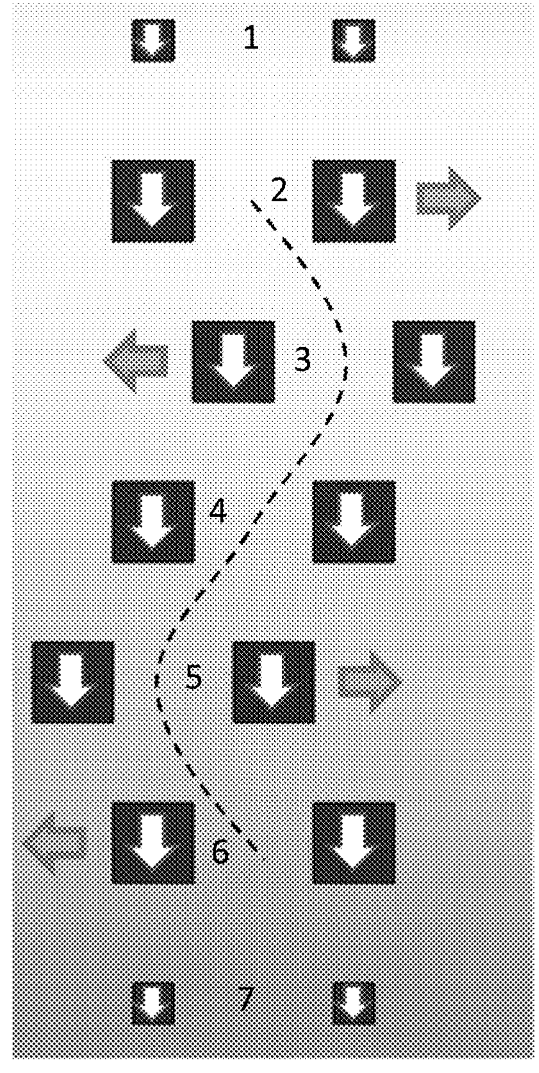
Figure 23B:
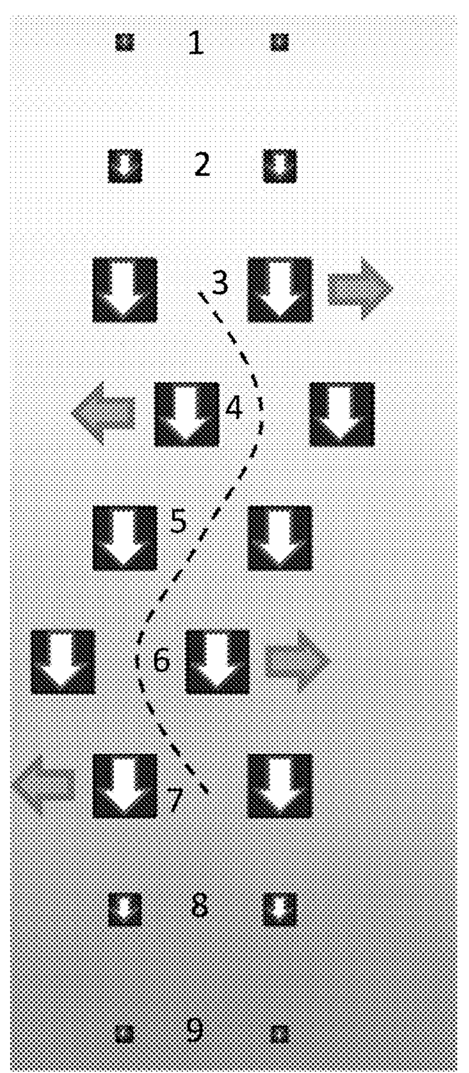

FIGS. 23A and 23B are configurations of implanted magnetic screw devices relative to 5-vertebrae-level abnormal S-type spinal curvatures, according to embodiments of the present invention, and as set forth in Example 6. The magnetic screw devices are positioned in the area of the abnormal S-type curvature, as well as in one or more one vertebra levels superior and inferior to the area of the abnormal S-type curvature, and at an offset distance of 20 mm. FIG. 23A is a configuration of implanted magnetic screw devices in vertebrae in the area of the abnormal S-type curvature, in one vertebra immediately superior to the area of the abnormal S-type curvature, and in one vertebra immediately inferior to the area of the abnormal S-type curvature. FIG. 23B is a configuration of implanted magnetic screw devices in vertebrae in the area of the abnormal S-type curvature, in two vertebrae immediately superior to the area of the abnormal S-type curvature, and in two vertebrae immediately inferior to the area of the abnormal S-type curvature. For each figure, the magnetic screw devices are implanted into both pedicles of each vertebra.

The vertical arrows depict the direction of the poles of the magnets of the magnetic screw devices, and the horizontal arrows depict the direction of the centering forces on the vertebrae.

Figure 24:
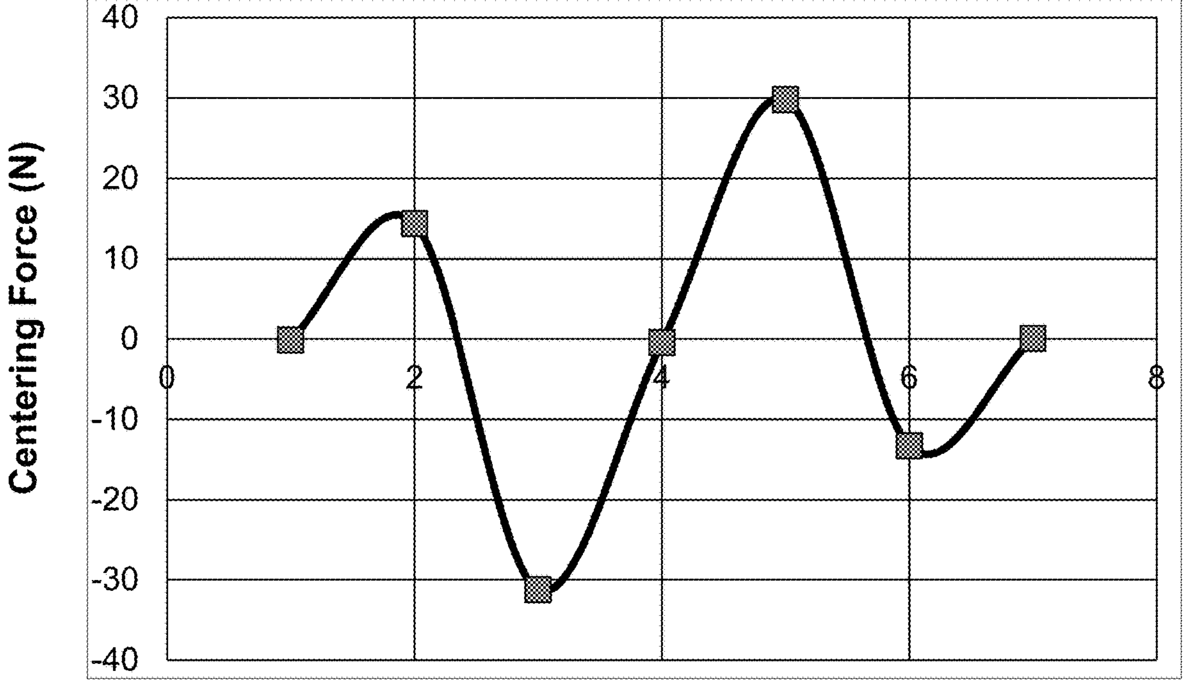

FIG. 24 is a plot of the centering forces generated at different vertebral levels by implanted magnetic screw devices that are positioned in the area of a 5-vertebrae-level abnormal S-type spinal curvature, one vertebra level immediately superior to the area of the curvature, and one vertebra level immediately inferior to the area of the curvature, according to embodiments of the present invention, and as set forth in Example 6. The magnetic screw devices are implanted at an offset distance of 20 mm, and in both pedicles of each vertebra.

Figure 25:
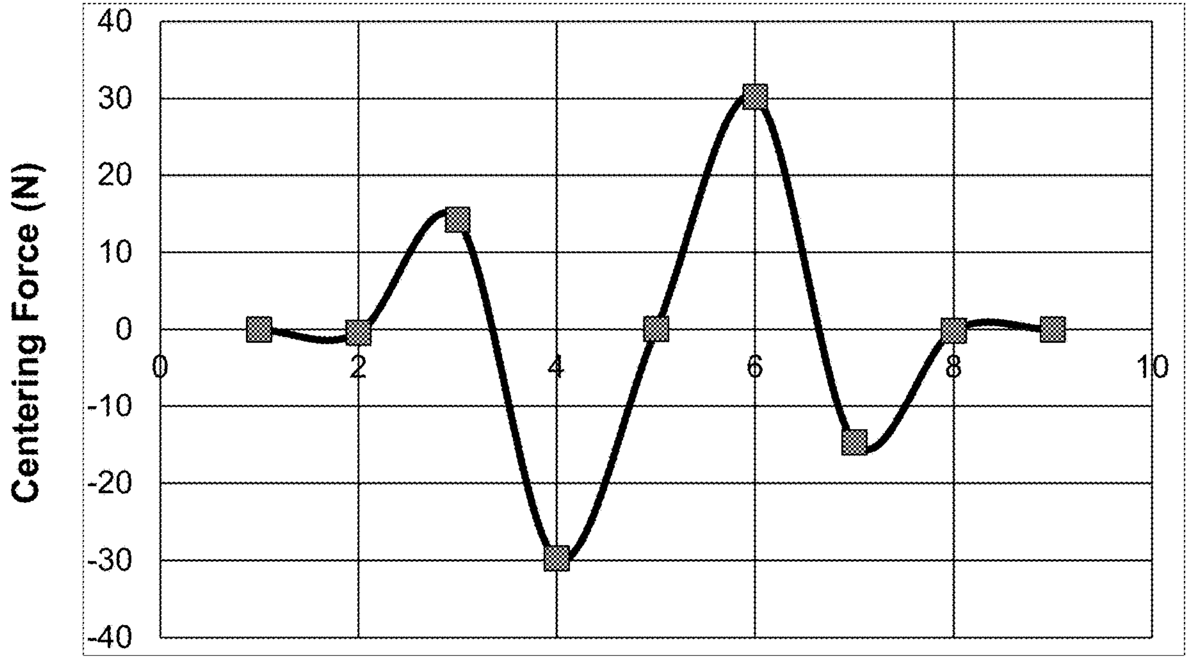

FIG. 25 is a plot of the centering forces generated at different vertebral levels by implanted magnetic screw devices that are positioned in the area of a 5-vertebrae-level abnormal S-type spinal curvature, two vertebrae levels immediately superior to the area of the curvature, and two vertebrae levels immediately inferior to the area of the curvature, according to embodiments of the present invention, and as set forth in Example 6. The magnetic screw devices are implanted at an offset distance of 20 mm, and in both pedicles of each vertebra.

Figure 26A:
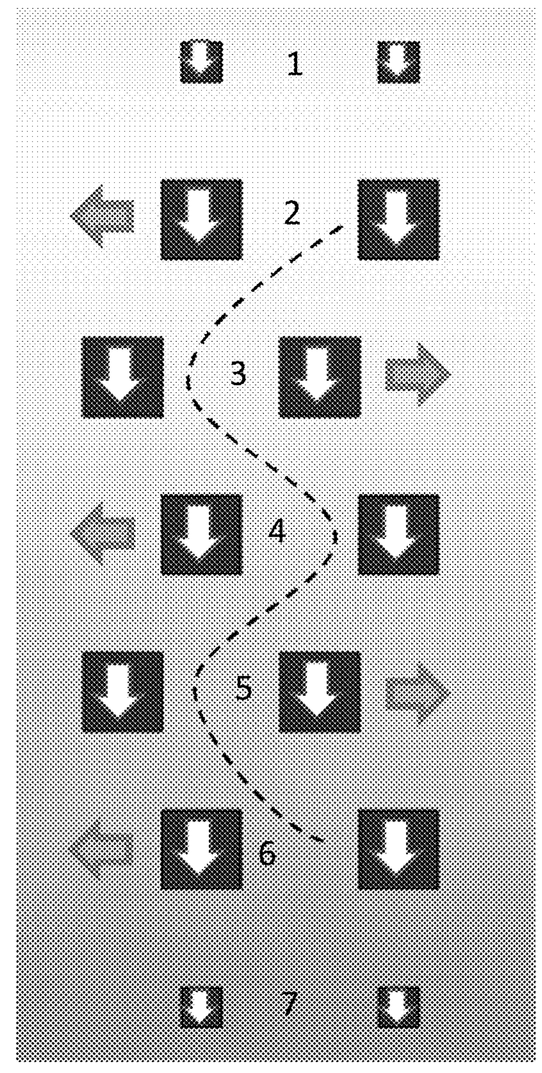
Figure 26B:
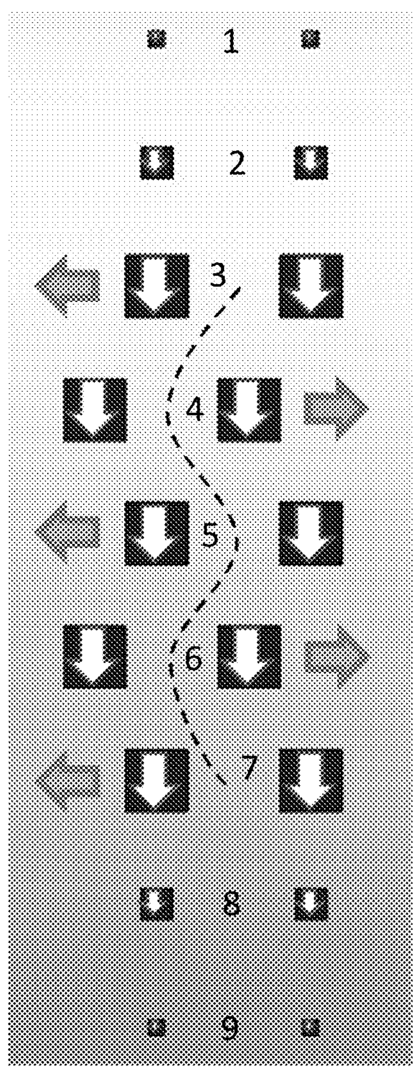

FIGS. 26A and 26B are configurations of implanted magnetic screw devices relative to 5-vertebrae-level abnormal double S-type spinal curvatures, according to embodiments of the present invention, and as set forth in Example 7. The magnetic screw devices are positioned in the area of the abnormal double S-type curvature, as well as in one or more one vertebra levels superior and inferior to the area of the abnormal double S-type curvature, and at an offset distance of 20 mm. FIG. 26A is a configuration of implanted magnetic screw devices in vertebrae in the area of the abnormal double S-type curvature, in one vertebra immediately superior to the area of the abnormal double S-type curvature, and in one vertebra immediately inferior to the area of the abnormal double S-type curvature. FIG. 26B is a configuration of implanted magnetic screw devices in vertebrae in the area of the abnormal double S-type curvature, in two vertebrae immediately superior to the area of the abnormal double S-type curvature, and in two vertebrae immediately inferior to the area of the abnormal double S-type curvature. For each figure, the magnetic screw devices are implanted into both pedicles of each vertebra. The vertical arrows depict the direction of the poles of the magnets of the magnetic screw devices, and the horizontal arrows depict the direction of the centering forces on the vertebrae.

Figure 27:
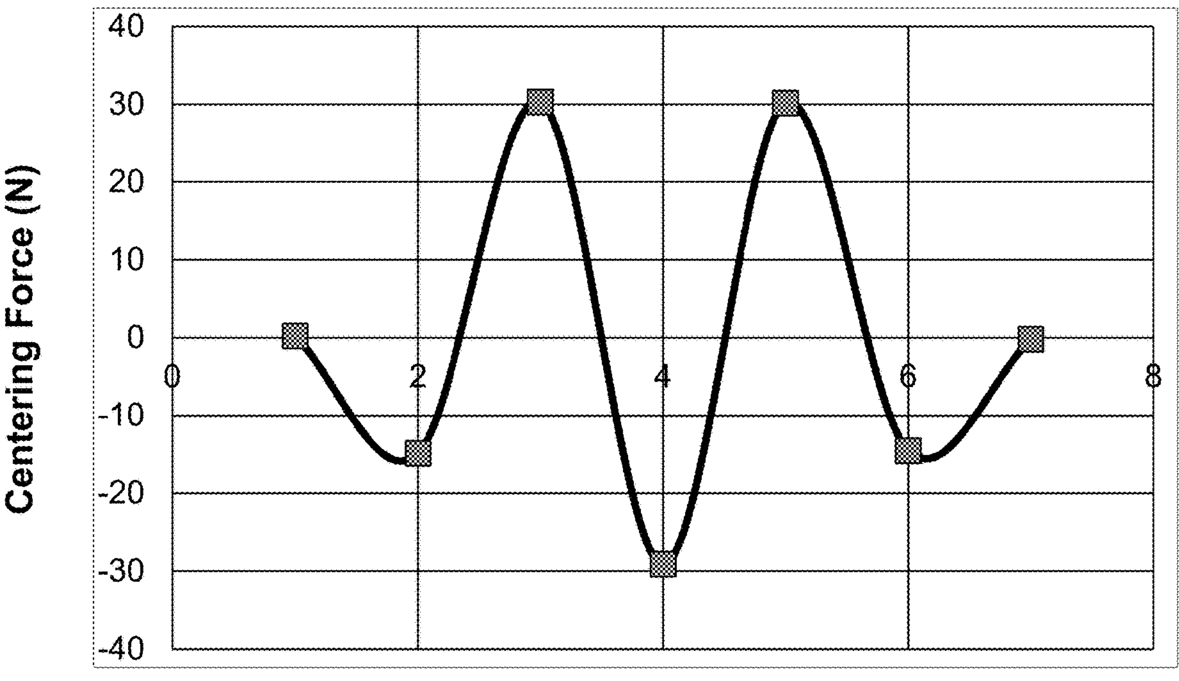

FIG. 27 is a plot of the centering forces generated at different vertebral levels by implanted magnetic screw devices that are positioned in the area of a 5-vertebrae-level abnormal double S-type spinal curvature, one vertebra level immediately superior to the area of the curvature, and one vertebra level immediately inferior to the area of the curvature, according to embodiments of the present invention, and as set forth in Example 7. The magnetic screw devices are implanted at an offset distance of 20 mm, and in both pedicles of each vertebra.

Figure 28:
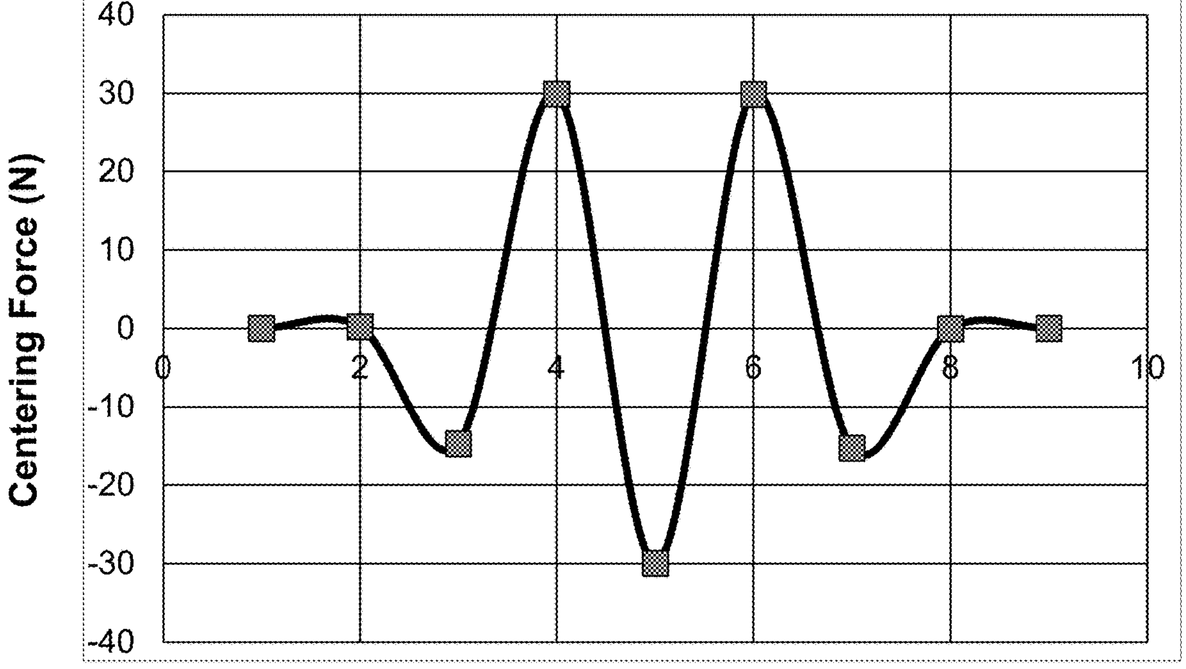

FIG. 28 is a plot of the centering forces generated at different vertebral levels by implanted magnetic screw devices that are positioned in the area of a 5-vertebrae-level abnormal double S-type spinal curvature, two vertebrae levels immediately superior to the area of the curvature, and two vertebrae levels immediately inferior to the area of the curvature, according to embodiments of the present invention, and as set forth in Example 7. The magnetic screw devices are implanted at an offset distance of 20 mm, and in both pedicles of each vertebra.

DETAILED DESCRIPTION OF THE INVENTION

The present invention relates to magnetic screw devices and methods of their use in spines with abnormal curvature. The magnetic screw devices of the present invention comprise magnets, which, upon implantation into different vertebrae of the spine, are oriented such that magnetic forces exist that compels the poles of the magnets to align, and in turn exerts a force that helps to straighten the curvature of the spine, resist those forces which tend to progress abnormal curvature over time, and/or maintain vertical alignment of the spine.

The methods of the present invention provide many advantages as compared to current treatments for abnormal spinal curvature. For example, relative to treatments such as fusion surgery, the methods of the present invention may be less invasive, which can lead to shorter recovery time; may have a lower risk of neurological complications; and may result in a smaller surgical scar. Another significant benefit of the present invention is that a brace will often not be required and, if used, would only provide additional assistance in spine stabilization and prevention of curve progression.

Magnetic Screw Device

An aspect of the invention relates to a magnetic screw device comprising a bone screw and one or more magnets.

Figure 1:
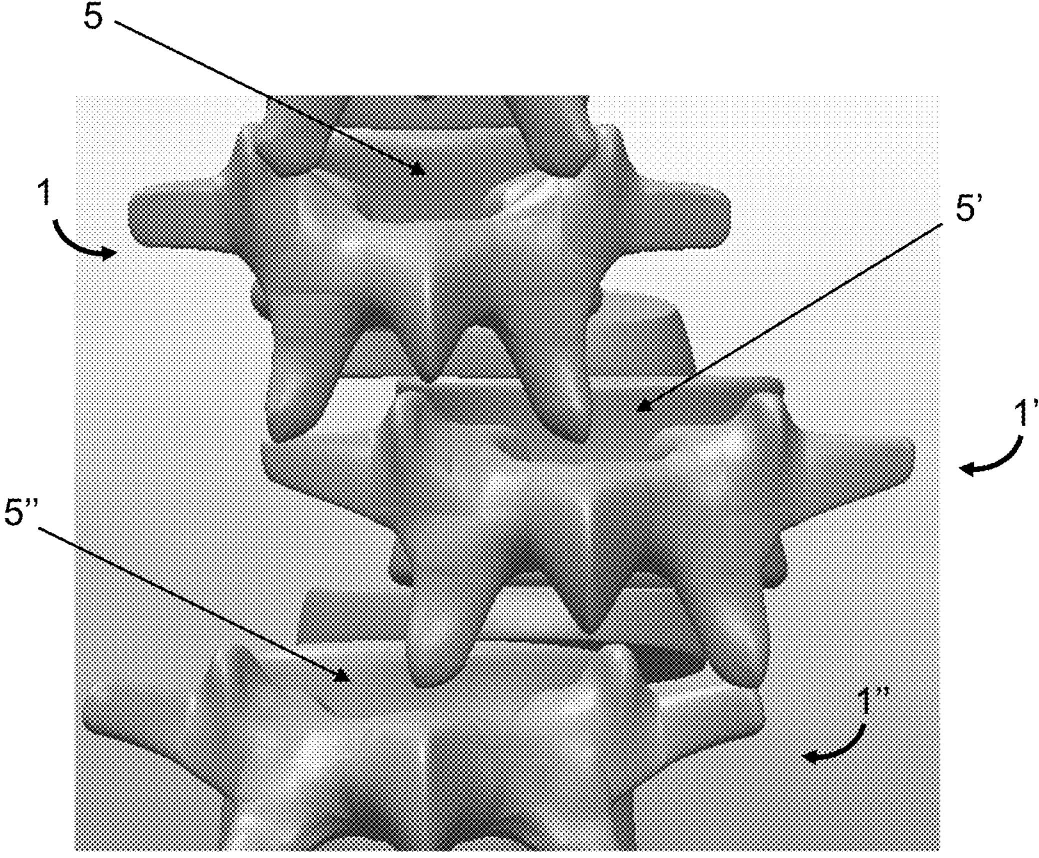
FIG. 1 is a posterior view of an abnormal curvature in the human spine.
Figure 2:
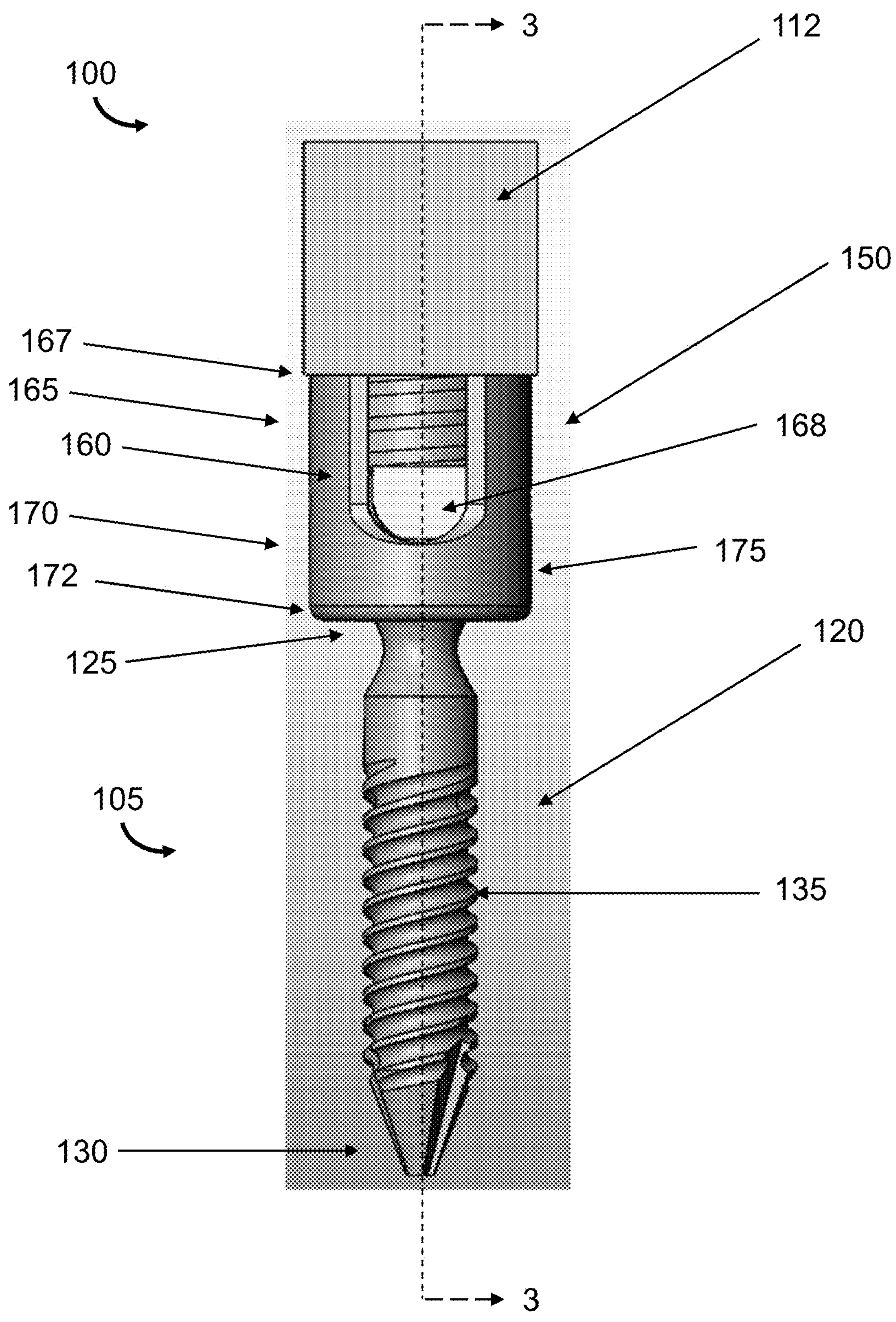
FIG. 2 is a lateral view of a magnetic screw device according to embodiments of the present invention.
Figure 3:
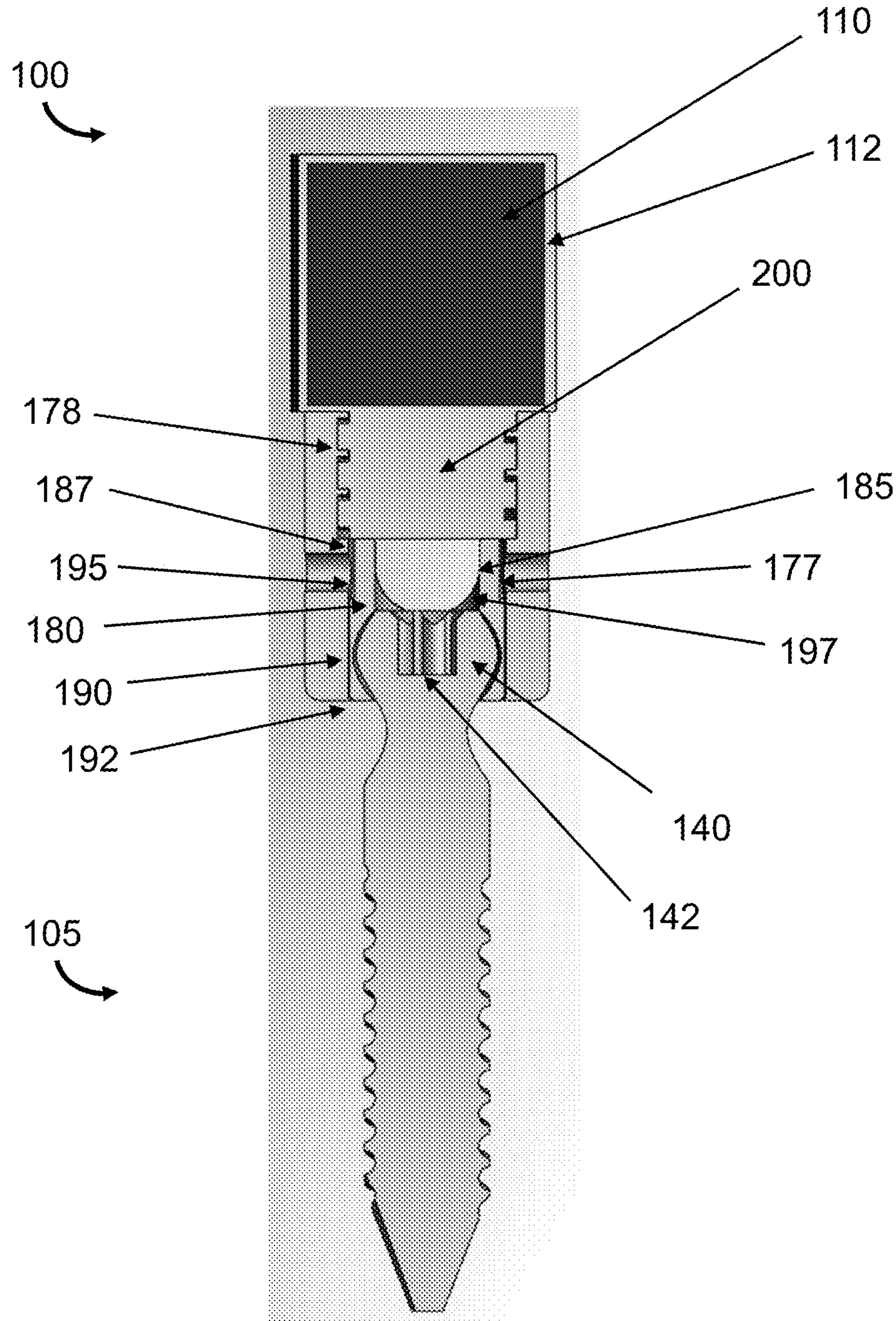
FIG. 3 is a cross-sectional view of a magnetic screw device according to embodiments of the present invention.

Embodiments of the magnetic screw device of the present invention are shown in FIGS. 2 and 3. The magnetic screw device 100 may comprise a bone screw 105 to which a magnet 110 is attached. The bone screw 105 comprises a stem 120 and a housing assembly 150. In some embodiments, the housing assembly 150 resembles a tulip. The stem 120 comprises an upper end 125, a lower end 130, and at least one thread 135 formed along the length of the stem 120. At the upper end 125 of the stem 120 may be a connector 140 that is configured to articulate with the housing assembly 150. The housing assembly 150 comprises an outer shell 160 and an inner shell 180. The outer shell 160 may comprise the general shape of a hollow cylinder that comprises an upper section 165 with an upper end 167, a lower section 170 with a lower end 172, an outer surface 175 and an inner surface 177. The inner shell 180 may comprise the general shape of a hollow cylinder that comprises an upper portion 185 with an upper end 187, a lower portion 190 with a lower end 192, an outer surface 195 and an inner surface 197.

The inner shell 180 may fit within, or may be concentric with, the lower section 170 of the outer shell 160, such that the lower end 172 of the outer shell 160 and the lower end 192 of the inner shell 180 are adjacent and the outer surface 195 of the inner shell 180 and the inner surface 177 of the lower section 170 of the outer shell 160 are fit together—in some embodiments, press-fit together, fused together, or otherwise adhered together.

The inner surface 197 of the lower portion 190 of the inner shell 180 may be configured to fit or form an articulating surface with the connector 140 of the stem 120. In some embodiments, the connector 140 may comprise a spherical or partially-spherical shape (e.g., the connector 140 may be generally spherical but with one or more flat surfaces) and the inner surface 197 of the inner shell 180 may comprise concave or partially concave curvatures that may resemble a socket or portion thereof. As a result, the stem 120 of the bone screw 105 may be capable of rotation and angulation relative to the housing assembly 150, due to the interaction between the connector 140 of the stem 120 and the inner surface 197 of the lower portion 190 of the inner shell 180. For example, the stem 120 may be able to rotate about the long axis of the stem 120 or angulate relative to the long axis of the housing assembly 150.

In some embodiments, the connector 140 may comprise a drive 142 on its top surface. The drive 142 is configured for insertion of a driver, such as 2.5 mm tapered hex driver. The drive 142 may also be configured for insertion of other types of drivers, for instance, Philips-head drivers or flat-head drivers.

The bone screw 105 may further comprise a set screw 200. At least a portion of the inner surface 177 of the upper section 165 of the outer shell 160 may comprise threads 178 for receipt of the set screw 200. Screwing the set screw into the outer shell 160 generates a compressive force on the connector 140, which prevents the connector's 140 movement within the housing assembly 150. Thus, the set screw 200 can function as a locking mechanism that maintains the stem 120 of the bone screw 105 at a set rotation and angulation relative to the housing assembly 150.

In some embodiments, the upper section 165 of the outer shell 160 may comprise one or more slots 168 that extend from the upper end 167 of the upper section 165 towards the lower end 172 of the lower section 170. These slots 168 may be U-shaped. In certain embodiments, there are at least two slots 168 that are located on opposite sides of the outer shell 160.

The at least one thread 135 on the stem 120 of the bone screw 105 may have a pitch, depth, and shape that are known in the art for threads of orthopaedic screws, including cortical and cancellous screws. For example, the thread 135 may have any shape as known in the art for drilling into bone, including but not limited to V-thread, buttress thread, reverse buttress, and square thread.

The stem 120 of the bone screw 105 may comprise a cross-sectional diameter of about 1 mm to about 10 mm, or about 2 mm to about 8 mm, or about 3 mm to about 6 mm. In some embodiments, the diameter of the stem 120, or a portion of the stem 120, may taper at an angle (not shown) of, for instance, about 1 degree or about 10 degrees towards the end of the lower section that is opposite to the head (i.e., forming the point of the bone screw). In some embodiments, only a portion of the stem 120 near the lower end 130 may taper at an angle. The length of the stem 120 may be about 10 mm to about 80 mm, or about 20 mm to about 60 mm.

The housing assembly 150 may comprise a diameter greater than the diameter of the stem 120.

The bone screw 105 may be fabricated with a metal alloy known in the art for orthopaedic applications, for example, titanium, cobalt chromium, or stainless steel. In some embodiments, the outer shell 160 and inner shell 180 of the housing assembly 150 may be fabricated as one continuous component. In other embodiments, the outer shell 160 and the inner shell 180 may be fabricated as a separate component that is attached or fastened or fit together.

In some embodiments, the stem 120 of the bone screw 105 may include an external textured surface (not shown), which enhances fixation of the bone screw 105 in bone and to aid in screw-bone interface stability. According to certain embodiments, plasma coating of a metal or ceramic may be applied to bone screw 105 to create the external textured surface.

The magnet 110 may be attached to the upper end 167 of the outer shell 160 or may be attached to the set screw 200. The magnet may be enclosed within a casing 112 to prevent exposure of the magnet to the environment inside the subject. The casing may comprise a metal alloy known in the art for orthopaedic applications, for example, titanium, cobalt chromium, or stainless steel. In some embodiments, the casing 112 may be continuous with the set screw 200, as shown in FIG. 3. In other embodiments, the casing 112 is attached (e.g., welded) or otherwise adhered to the set screw 200 (not shown).

The magnet 110 may comprise a shape that generally resembles a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. The height of the magnet 110, which is measured by the distance that the magnet extends from the housing assembly 150, may be about 2 mm to about 30 mm, or about 5 mm to about 20 mm. The diameter or width/depth, as measured perpendicular to the height, may be about 2 mm to about 30 mm, or about 5 mm to about 20 mm.

In alternative embodiments, the magnetic screw device may comprise a magnet attached to bone screws that are known in the art, in particular pedicle bone screws. Such bone screws include those that are described in U.S. Pat. Nos. 5,549,608; 5,569,247; 5,800,435; 6,485,491; 6,716,214; 7,066,937; 7,625,396; 7,682,377; 8,197,518; U.S. Patent Publication No. 2008/0177322; and U.S. Patent Publication No. 2017/0020573; each of which is incorporated herein by reference.

The magnet of the present invention may comprise materials known in the art. For example, the magnets may be iron-based, nickel-based, cobalt-based, or an alloy of rare-earth metals. In certain embodiments, the magnets may be a rare-earth magnet, which generally has strong attraction and repulsion forces and have high retentive capacity and resistance to demagnification. In a preferred embodiment, the rare-earth magnet is an alloy of neodymium, iron, and boron ("NdFeB"). NdFeB magnets provide strong permanent magnetism, high retentive capacity, and resistance to demagnetization.

Treatment of Spine with an Abnormal Curvature

The magnetic screw device of the present invention may be used to address or help treat a spine with an abnormal curvature.

Therefore, aspects of the present invention are directed to (i) a method of treating a spine with an abnormal curvature; (ii) a method of stabilizing a spine with an abnormal curvature; (iii) a method of correcting an abnormal curvature in a spine over time; (iv) a method of preventing curve progression of a spine with an abnormal curvature; (v) a method of reducing the risk of curve progression of a spine with an abnormal curvature; or (vi) a method of aligning vertebrae in a spine with an abnormal curvature; or (vii) a method of aiding the realignment of a spine with an abnormal curvature. Aspects of the invention are also directed to the use of a magnetic screw device of the present invention to (i) treat a spine with an abnormal curvature; (ii) stabilize a spine with an abnormal curvature; (iii) correct an abnormal curvature in a spine over time; (iv) prevent curve progression of a spine with an abnormal curvature; (v) reduce the risk of curve progression of a spine with an abnormal curvature; or (vi) align vertebrae in a spine with an abnormal curvature; or (vii) aid the realignment of a spine with an abnormal curvature. Further aspects of the invention are directed to a magnetic screw device of the present invention for use in (i) treating a spine with an abnormal curvature; (ii) stabilizing a spine with an abnormal curvature; (iii) correcting an abnormal curvature in a spine over time; (iv) preventing curve progression of a spine with an abnormal curvature; (v) reducing the risk of curve progression of a spine with an abnormal curvature; or (vi) aligning vertebrae in a spine with an abnormal curvature; or (vii) aiding the realignment of a spine with an abnormal curvature.

The methods and uses of the present invention may be applied to spinal curvatures that are at least about 10 degrees, or at least 15 degrees, or at least about 20 degrees, or at least about 25 degrees, or at least about 30 degrees, or at least about 35 degrees, or at least about 40 degrees, or at least about 45 degrees, or at least about 50 degrees, or at least about 55 degrees, or at least about 60 degrees, or about 65 degrees, as determined using the Cobb method of measuring the degree of scoliosis. In some embodiments, the methods and uses of the present invention may be applied to spinal curvatures that are about 10 degrees to about 60 degrees, such as about 10 degrees to about 25 degrees, or about 25 degrees to about 45 degrees, or about 45 degrees to about 65 degrees, as determined using the Cobb method of measuring the degree of scoliosis.

In embodiments of the invention, these methods and uses may comprise implanting one or more of the magnetic screw devices of the present invention in one or both pedicles of one or more vertebrae.

The magnetic screw devices may be implanted into one pedicle of each vertebra. Alternatively, the magnetic screw devices may be implanted into both pedicles of each vertebra. The magnet screw devices may be implanted such that the stem of the magnetic screw devices is generally perpendicular to the long axis of the spine.

The magnetic screw devices may be implanted into two or more vertebrae. In some embodiments, the magnetic screw devices may be implanted into two or more vertebrae in the area of the abnormal curvature in the spine. In some embodiments, the magnetic screw devices may be implanted into one or more vertebrae in the area of the abnormal curvature of the spine, and into one or more adjacent vertebrae. In certain embodiments, the magnetic screw devices may be implanted into two or more vertebrae, wherein at least one of the vertebrae is in the area of the abnormal curvature of the spine, and at least one of the vertebrae is not in the area of the abnormal curvature of the spine.

The magnetic screw devices may be implanted into adjacent vertebrae and, in some embodiments, in more than two adjacent vertebrae. In certain embodiments, the magnetic screw devices may be implanted into two or more vertebrae that are in the area in which the spine curves abnormally, and, in some embodiments, in the vertebrae directly adjacent to the curve(s).

In certain embodiments, the magnetic screw devices may be implanted into the adjacent vertebrae that are in the area of the abnormal spinal curvature, into an adjacent vertebra immediately superior to the vertebrae in the area of the abnormal spinal curvature, and into an adjacent vertebra immediately inferior to the vertebrae in the area of the abnormal spinal curvature.

In certain embodiments, the magnetic screw devices may be implanted into the adjacent vertebrae that are in the area of the abnormal spinal curvature, into two adjacent vertebrae immediately superior to the vertebrae in the area of the abnormal spinal curvature, and into two adjacent vertebrae immediately inferior to the vertebrae in the area of the abnormal spinal curvature.

In some embodiments, the methods and uses may further comprise manually orienting the housing assembly of each implanted magnetic screw device so that the magnetic poles of the magnet in each magnetic screw device are aligned, imparting either an attractive or repulsive force. For each magnetic screw device, this may involve rotating and/or angling the housing assembly relative to the stem of the magnetic screw device in order to orient the attached magnet to align its magnetic pole with the magnetic poles of the magnets of the other implanted magnetic screw devices. In some embodiments, the magnetic poles of the magnets of each of the magnetic screw devices are all oriented in a vertical direction, i.e., in the direction of the long axis of the spine.

In other embodiments, the methods and uses may be performed without manually orienting the house assembly of each implanted magnetic screw device. In such embodiments, the magnetic pole of the magnet in the housing assembly of each magnetic device may self-align, resulting in the magnetic poles of the magnets in the housing assemblies of the implanted magnetic devices being in alignment.

The centering force (i.e., the force compelling the vertebrae to align) that is generated from the presence of the magnets is affected by the number of magnets implanted, the magnet offset (angle of curvature) present in the spine, as well as the strength of the individual magnets, which is controlled in part by the shape and size of the magnets. But the magnetic force field generated by the magnetic poles of each of the magnets being in the same direction can result in an attempted vertical alignment of the magnets, and consequently an attempted vertical alignment or stacking of the vertebral bodies into which the magnetic devices are implanted.

In some embodiments, the placement of the magnetic screw devices and the orientation of their housing assemblies relative to each other may be predetermined based on imaging (such as radiographic imaging) of the spine and measurements of the deformity (such as degrees of scoliosis using the Cobb method).

An example of implanting magnetic screw devices into vertebrae of a spine with abnormal curvature is shown in FIGS. 4A and 4B. These figures show a magnetic screw device 100, 100', and 100" implanted into each left pedicle 10A, 10A', and 10A", respectively, and each right pedicle 10B, 10B', and 10B", respectively, of three adjacent vertebrae 1, 1', and 1", respectively. The magnets 110, 110', and 110" of each magnetic screw device 100, 100', and 100", respectively, are oriented so that the magnetic poles (depicted by the white arrows) of the magnets 110, 110', and 110" are in the same direction.

In certain embodiments, to treat an abnormal C-type curvature of the spine, magnetic screw devices may be implanted in one pedicle (for example, see FIGS. 8A and 9A) or both pedicles of each vertebra (for example, see FIGS. 8B and 9B). In some embodiments, magnetic screw devices may be implanted in the vertebra at the base of the abnormal C-type curve (e.g., most inferior vertebra in the abnormal C-type curve) only (not shown) or in the vertebra at the top of the abnormal C-type curve (e.g., most superior vertebra in the abnormal C-type curve) only (not shown); in each vertebra of the abnormal C-type curve (for example, see FIGS. 8A, 8B, 9A, 9B); in each vertebra of the abnormal C-type curve and in one vertebra superior and/or inferior to the abnormal C-type curve (for example, see FIG. 20A); or in each vertebra of the abnormal C-type curve and in more than one vertebra superior and/or inferior to the abnormal C-type curve (for example, see FIG. 20B).

In certain embodiments, to treat an abnormal S-type curvature of the spine, magnetic screw devices may be implanted in one pedicle (for example, see FIGS. 12A and 13A) or both pedicles of each vertebra (for example, see FIGS. 12B and 13B). In some embodiments, magnetic screw devices may be implanted in the vertebra at the base of the abnormal S-type curve (e.g., most inferior vertebra in the abnormal S-type curve) only (not shown) or in the vertebra at the top of the abnormal S-type curve (e.g., most superior vertebra in the abnormal S-type curve) only (not shown); in each vertebra of the abnormal S-type curve (for example, see FIGS. 12A, 12B, 13A, 13B); in each vertebra of the abnormal S-type curve and in one vertebra superior and/or inferior to the abnormal S-type curve (for example, see FIG. 23A); or in each vertebra of the abnormal S-type curve and in more than one vertebra superior and/or inferior to the abnormal S-type curve (for example, see FIG. 23B).

In certain embodiments, to treat an abnormal double S-type curvature of the spine, magnetic screw devices may be implanted in one pedicle (for example, see FIGS. 16A and 17A) or both pedicles of each vertebra (for example, see FIGS. 16B and 17B). In some embodiments, magnetic screw devices may be implanted in the vertebra at the base of the abnormal double S-type curve (e.g., most inferior vertebra in the abnormal double S-type curve) only (not shown) or in the vertebra at the top of the abnormal double S-type curve (e.g., most superior vertebra in the abnormal double S-type curve) only (not shown); in each vertebra of the abnormal double S-type curve (for example, see FIGS. 16A, 16B, 17A, 17B); in each vertebra of the abnormal double S-type curve and in one vertebra superior and/or inferior to the abnormal double S-type curve (for example, see FIG. 26A); or in each vertebra of the abnormal double S-type curve and in more than one vertebra superior and/or inferior to the abnormal double S-type curve (for example, see FIG. 26B).

In some embodiments, implantation of magnetic screw devices superior and inferior to the abnormal spinal curve may help mitigate the vertical load (loading in the direction of the mid-line axis of the spine) on the vertebrae in the abnormal spinal curve and, in some embodiments, on the vertebrae superior and/or inferior to the abnormal spinal curve. To this end, embodiments of the present invention relate to a method of mitigating vertical load in vertebrae of a spine undergoing treatment for an abnormal spinal curvature, the method comprising implanting magnetic screw devices according to embodiments of the invention as described herein.

The shape, size, and thickness of the magnets of the magnetic screw device may be selected based upon anatomical consideration, the distance between the pedicles and vertebral bodies, as well as overlying soft tissue and musculature in order to achieve the force desired. For example, as discussed herein, the magnets may comprise a shape that generally resembles a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. The height of the magnets, which is measured by the distance that the magnet extends from the housing assembly, may be about 2 mm to about 30 mm, or about 5 mm to about 20 mm. The diameter or width/depth, as measured perpendicular to the height, may be about 2 mm to about 30 mm, or about 5 mm to about 20 mm.

The shape, size, and thickness of the magnets of the magnetic screw devices may differ among the magnetic screw devices that are implanted. For instance, the magnets of the magnetic screw devices within the abnormal curvature of the spine may be of a particular shape, size, and/or thickness, or a particular strength, and the magnets of the magnetic screw devices superior and/or inferior the abnormal curvature of the spine may be of a different shape, size, and/or thickness, or a different strength (e.g., the magnets above and/or below the abnormal curvature may be smaller and/or have a lower strength, or they may be larger and and/or have greater strength). In some embodiments, the magnets of the magnetic screw devices superior and/or inferior to the abnormal curvature of the spine may comprise a magnetic strength that is about 10% to 90%, such as about 10%, or about 20%, or about 30%, or about 40%, or about 50%, or about 60%, or about 70%, or about 80%, or about 90%, of the magnetic strength of the magnets of the magnetic screw devices within the abnormal curvature of the spine. In certain embodiments, the magnets of the magnetic screw devices implanted in the vertebra that is one vertebral level superior (immediately superior) and in the vertebra that is one vertebral level inferior (immediately inferior) to the abnormal curvature of the spine may comprise a magnetic strength that is the same or about 1% to 90%, or about 10% to about 80%, such as about 1%, or about 2%, or about 3%, or about 4%, or about 5%, or about 6%, or about 7%, or about 8%, or about 9%, or about 10%, or about 11%, or about 12%, or about 13%, or about 14%, or about 15%, or about 20%, or about 30%, or about 40%, or about 50%, or about 60%, or about 70%, or about 80%, or about 90%, of the magnetic strength of the magnets of the magnetic screw devices within the abnormal curvature of the spine; and the magnets of the magnetic screw devices implanted in the vertebra that is two vertebral levels superior and in the vertebra that is two vertebral levels inferior to the abnormal curvature of the spine may comprise a magnetic strength that is the same or about 1% to 90%, or about 10% to about 80%, such as about 1%, or about 2%, or about 3%, or about 4%, or about 5%, or about 6%, or about 7%, or about 8%, or about 9%, or about 10%, or about 11%, or about 12%, or about 13%, or about 14%, or about 15%, or about 20%, or about 30%, or about 40%, or about 50%, or about 60%, or about 70%, or about 80%, or about 90%, of the magnetic strength of the magnets of the magnetic screw devices implanted in the vertebra that is one vertebral level superior and in the vertebra that is one vertebral level inferior to the abnormal curvature of the spine.

In embodiments of the present invention, an external brace may be used in conjunction with the magnetic screw devices. The external brace may provide an attractive straightening force to stabilize the spine and prevent further progression of the abnormal curvature. The external brace may comprise one or more magnets, which can be larger than the magnets used in the magnetic screw devices. With the use of the external brace, magnetic screw devices do not have to be implanted in both pedicles of a vertebra or in each of the vertebrae that are located in the area of the abnormal curvature or adjacent thereto. In other embodiments, the external brace may not have any magnets and may be used to provide additional support to the spine.

In some embodiments, the combination of implanting one or more magnetic screw devices and having the subject wear an external brace may be used to provide more complex straightening loading in highly distorted abnormal three-dimensionally curved spines, because greater diversity in placement can be utilized internally and externally in the brace.

EXAMPLES

The following examples used modeling to assess the centering forces generated by implanted magnetic screw devices for different types of abnormal spinal curvatures. As demonstrated in FIG. 5, the relative positioning of the magnets 110 of the implanted magnetic devices 100 was characterized by the offset distance 300, which largely reflects the severity of the abnormal curvature, and the horizontal separation 305 and vertical separation 310, which is largely based on the anatomic dimensions of the vertebrae and the spine.

The centering forces were modeled using JMAG simulation technology. JMAG utilizes finite element analysis to calculate the magnetic forces and fields. Briefly, the geometry of the magnets is loaded into the simulation software, and the magnetic strength and pole orientation is assigned when the simulation is performed.

Example 1

This study analyzed the centering force generated by magnetic screw devices implanted in three adjacent vertebrae that were in the area of an abnormal C-type spinal curvature, as shown in FIG. 7. The analysis considered different offset distances and the impact of implanting the magnetic screw devices in one or both pedicles of each vertebra. The analysis was conducted for magnetic screw devices comprising a 2 cm×2 cm×2 cm magnet, and implanted with a horizontal separation of 50 mm and a vertical separation of 40 mm.

The results, presented in FIG. 7 and Table 1, show that centering force at vertebral level 2 (middle vertebra of the abnormal curvature) increases as the offset distance increases until the offset distance exceeds 20 mm, at which point the centering force begins to decrease. Implantation of a magnetic screw device into both pedicles of each vertebra generated a greater centering force than the implantation of a magnetic screw device into one pedicle of each vertebra, except when the offset distance was at 20 mm.

TABLE 1

Centering forces generated by magnetic screw devices in a 3-level abnormal spinal C-curve with variations in offset distance.

| Offset | | Centering Force (N) | |
|---|---|---|---|
| (mm) | (degrees) | One Device Per Vertebra | Two Devices Per Vertebra |
| 0 | 0 | 0.05 | 0.72 |
| 10 | 14 | 15.70 | 28.04 |
| 20 | 27 | 17.53 | 24.85 |
| 30 | 37 | 10.89 | 6.14 |

Example 2

This study analyzed the centering forces generated by magnetic screw devices implanted in five adjacent vertebrae that were in the area of an abnormal C-type spinal curvature. The analysis considered the impact of implanting the magnetic screw devices in one or both pedicles of each vertebra. The analysis was conducted for magnetic screw devices comprising a 2 cm×2 cm×2 cm magnet, and implanted in one of the following positions: (i) an offset distance of 10 mm (14°), a horizontal separation of 50 mm, and a vertical separation of 40 mm, as illustrated in FIGS. 8A (implanted into one pedicle) and 8B (both pedicles); or (ii) an offset distance of 20 mm (27°), a horizontal separation of 50 mm, and a vertical separation of 40 mm, as illustrated in FIGS. 9A (implanted into one pedicle) and 9B (both pedicles).

The results, presented in FIGS. 10 and 11 and in Table 2, show that the greatest centering force was generated at vertebral level 3 (middle vertebra of the abnormal curvature), but centering forces were also generated at vertebral levels 1 and 5 (vertebrae at the superior end and the inferior end, respectively, of the abnormal curvature). The centering force at vertebral level 3 was nearly twice in magnitude as compared to the centering forces at vertebral levels 1 and 5.

Implantation of a magnetic screw device into both pedicles of each vertebra generated a greater centering force than the implantation of a magnetic screw device into one pedicle of each vertebra. Further, in general, when a magnetic screw device was implanted into both pedicles of each vertebra, the centering force decreased as the offset distance increased. In contrast, when a magnetic screw device was implanted into one pedicle of each vertebra, the centering force increased as the offset distance increased.

TABLE 2

Centering forces generated by magnetic screw devices implanted in one or both pedicles of adjacent vertebrae in a 5-level abnormal spinal C-curve.

| | Centering Force (10 mm offset distance) | | Centering Force (20 mm offset distance) | |
|---|---|---|---|---|
| Level | Implant into One Pedicle | Implant into Both Pedicles | Implant into One Pedicle | Implant into Both Pedicles |
| 1 | −8.63N | −14.6N | −9.52N | −13.50N |
| 2 | 0.08N | −0.01N | −0.07N | −0.04N |
| 3 | 17.36N | 29.07N | 18.98N | 26.55N |
| 4 | 0.19N | 0.29N | −0.01N | 0.10N |
| 5 | −8.67N | −14.48N | −9.55N | −13.49N |

Example 3

This study analyzed the centering forces generated by magnetic screw devices implanted in five adjacent vertebrae that were in the area of an abnormal S-type spinal curvature. The analysis considered the impact of implanting the magnetic screw devices in one or both pedicles of each vertebra. The analysis was conducted for magnetic screw devices comprising a 2 cm×2 cm×2 cm magnet, and implanted in one of the following positions: (i) an offset distance of 10 mm (14°), a horizontal separation of 50 mm, and a vertical separation of 40 mm, as illustrated in FIGS. 12A (implanted into one pedicle) and 12B (both pedicles); or (ii) an offset distance of 20 mm (27°), a horizontal separation of 50 mm, and a vertical separation of 40 mm, as illustrated in FIGS. 13A (implanted into one pedicle) and 13B (both pedicles).

The results, presented in FIGS. 14 and 15 and in Table 3, show that the greatest centering force was generated at vertebral levels 2 and 4 (vertebrae immediately superior and inferior, respectively, to the middle of the abnormal curvature), but centering forces were also generated at vertebral levels 1 and 5 (vertebrae at the superior end and the inferior end, respectively, of the abnormal curvature). The centering forces at vertebral levels 2 and 4 were each about twice in magnitude as compared to the centering forces at vertebral levels 1 and 5.

Implantation of a magnetic screw device into both pedicles of each vertebra generated a greater centering force than the implantation of a magnetic screw device into one pedicle of each vertebra. Further, in general, when a magnetic screw device was implanted into both pedicles of each vertebra, the centering force decreased as the offset distance increased. In contrast, when a magnetic screw device was implanted into one pedicle of each vertebra, the centering force increased as the offset distance increased.

TABLE 3

Centering forces generated by magnetic screw devices implanted in one or both pedicles of adjacent vertebrae in a 5-level abnormal spinal S-curve.

| | Centering Force (10 mm offset distance) | | Centering Force (20 mm offset distance) | |
|---|---|---|---|---|
| Level | Implant into One Pedicle | Implant into Both Pedicles | Implant into One Pedicle | Implant into Both Pedicles |
| 1 | 8.11N | 13.71N | 8.82N | 12.17N |
| 2 | −16.56N | −28.29N | −18.47N | −25.97N |
| 3 | 0.07N | 0.24N | −0.10N | −0.01N |
| 4 | 16.66N | 28.54N | 18.58N | 26.04N |
| 5 | −7.94N | −13.81N | −8.87N | −12.23N |

Example 4

This study analyzed the centering forces generated by magnetic screw devices implanted in five adjacent vertebrae that were in the area of an abnormal double S-type spinal curvature. The analysis considered the impact of implanting the magnetic screw devices in one or both pedicles of each vertebra. The analysis was conducted for magnetic screw devices comprising a 2 cm×2 cm×2 cm magnet, and implanted in one of the following positions: (i) an offset distance of 10 mm (14°), a horizontal separation of 50 mm, and a vertical separation of 40 mm, as illustrated in FIGS. 16A (implanted into one pedicle) and 16B (both pedicles); or (ii) an offset distance of 20 mm (27°), a horizontal separation of 50 mm, and a vertical separation of 40 mm, as illustrated in FIGS. 17A (implanted into one pedicle) and 17B (both pedicles).

The results, presented in FIGS. 18 and 19 and in Table 4, show that the greatest centering force was generated at vertebral levels 2, 3, and 4 (vertebrae immediately superior to the middle of the abnormal curvature, middle vertebra of the abnormal curvature, and vertebra immediately inferior to the middle of the abnormal curvature, respectively), but centering forces were also generated at vertebral levels 1 and 5 (vertebrae at the superior end and the inferior end, respectively, of the abnormal curvature). The centering forces at vertebral levels 2, 3, and 4 were each about twice in magnitude as compared to the centering forces at vertebral levels 1 and 5.

Implantation of a magnetic screw device into each pedicle of each vertebra generated a greater centering force than the implantation of a magnetic screw device into one pedicle of each vertebra. Further, in general, when a magnetic screw device was implanted into both pedicles of each vertebra, the centering force decreased as the offset distance increased. In contrast, when a magnetic screw device was implanted into one pedicle of each vertebra, the centering force increased as the offset distance increased.

TABLE 4

Centering forces generated by magnetic screw devices implanted in one or both pedicles of adjacent vertebrae in a 5-level abnormal spinal double S-curve.

| | Centering Force (10 mm offset distance) | | Centering Force (20 mm offset distance) | |
|---|---|---|---|---|
| Level | Implant into One Pedicle | Implant into Both Pedicles | Implant into One Pedicle | Implant into Both Pedicles |
| 1 | −8.17N | −13.76N | −9.01N | −12.51N |
| 2 | 15.97N | 27.85N | 18.07N | 24.98N |
| 3 | −16.13N | −28.03N | −18.07N | −24.91N |
| 4 | 15.99N | 27.62N | 18.03N | 25.13N |
| 5 | −8.19N | −13.99N | −9.12N | −12.67N |

Example 5

This study analyzed both the centering forces and vertical forces generated by implanting additional magnetic screw devices into both pedicles of vertebrae superior and inferior to the area of an abnormal C-type spinal curvature. The study considered implantation of magnetic screw devices in the following two arrangements: (1) implantation into seven adjacent vertebrae—five vertebrae in the area of an abnormal C-type curvature, one vertebra superior to the abnormal C-type curvature, and one vertebra inferior to the abnormal C-type curvature (see FIG. 20A); and (2) implantation into nine adjacent vertebrae—five vertebrae in the area of an abnormal C-type curvature, two vertebrae superior to the abnormal C-type curvature, and two vertebrae inferior to the abnormal C-type curvature (see FIG. 20B).

Under the analysis, the magnetic screw devices in the area of the abnormal C-type curvature (vertebral levels 2 to 6 in FIG. 20A; vertebral levels 3 to 7 in FIG. 20B) comprised a 2 cm×2 cm×2 cm magnet, and the magnetic screw devices immediately superior and immediately inferior to the area of the abnormal C-type curvature (vertebral levels 1 and 7 in FIG. 20A; vertebral levels 2 and 8 in FIG. 20B) comprised a 1 cm×1 cm×1 cm magnet (which has 12.5% of the magnetic strength of the 2 cm×2 cm×2 cm magnet). For arrangement (2) in which two magnetic screw devices are implanted both superior and inferior to the area of the abnormal C-type curvature, the magnetic screw devices at the superior and inferior ends (vertebral levels 1 and 9 in FIG. 20B) comprised a 0.5 cm×0.5 cm×0.5 cm magnet (which has 12.5% of the magnetic strength of the 1 cm×1 cm×1 cm magnet; and 1.6% of the magnetic strength of the 2 cm×2 cm×2 cm magnet). The offset distance between the vertebrae in the area of the abnormal curvature was 20 mm (27°). The magnetic screw devices superior to the area of the abnormal C-type curvature (vertebral level 1 in FIG. 20A; vertebral levels 1 and 2 in FIG. 20B) were aligned with the superior-most magnetic screw device in the area of the abnormal C-type curvature (vertebral level 2 in FIG. 20A; vertebral level 3 in FIG. 20B), and the magnetic screw devices inferior to the area of the abnormal C-type curvature (vertebral level 7 in FIG. 20A; vertebral levels 8 and 9 in FIG. 20B) were aligned with the inferior-most magnetic screw device in the area of the abnormal C-type curvature (vertebral level 6 in FIG. 20A; vertebral level 7 in FIG. 20B).

The results of the analysis are shown in FIGS. 21 and 22 and in Tables 5 and 6. For both arrangements of implanted magnetic screw devices (one vertebra superior and inferior to the area of abnormal C-type curvature, or two vertebrae superior and inferior to the area of abnormal C-type curvature), the greatest centering force was generated at the vertebra in the middle of the area of the abnormal C-type curvature (vertebral level 4 in FIG. 20A; vertebral level 5 in FIG. 20B), but centering forces were also generated in vertebrae at the superior end and the inferior end of the area of the abnormal C-type curvature (vertebral levels 2 and 6, respectively, in FIG. 20A; vertebral levels 3 and 7, respectively, in FIG. 20B). The centering force at the middle vertebra of the area of the abnormal C-type curvature was nearly twice in magnitude as compared to the centering forces at the vertebrae at the superior end and the inferior end of the area of the abnormal C-type curvature (see FIGS. 21 and 22, and Table 5).

This pattern is similar to the centering forces that resulted in the study described in Example 2, in which magnetic screw devices were implanted in five adjacent vertebrae in the area of an abnormal C-type spinal curvature only. A comparison between the results of Example 2 and the results of the present Example 5 shows that the centering force on the vertebra in the middle of the abnormal curvature (vertebral level 3 in FIG. 9B of Example 2; vertebral level 4 in FIG. 20A and vertebral level 5 in FIG. 20B of the present Example 5) and the centering forces on the vertebrae at the ends of the area of the abnormal curvature (vertebral levels 1 and 5 in FIG. 9B of Example 2; vertebral levels 2 and 6 in FIG. 20A and vertebral levels 3 and 7 of FIG. 20B of the present Example 5) were greater in the present Example 5, which suggests that the presence of the small magnets superior and inferior to the area of the abnormal C-type curvature elevates the magnitude of the centering forces experienced by the magnetic screw devices within the area of the abnormal C-type curvature.

TABLE 5

Centering forces generated by magnetic screw devices implanted in both pedicles of adjacent vertebrae in 7-level and 9-level abnormal C-type curvature.

| | Arrangement (1) 7 Adjacent Vertebrae | | Arrangement (2) 9 Adjacent Vertebrae | |
|---|---|---|---|---|
| Level | Level # | Centering Force | Level # | Centering Force |
| Superior | | | 1 | −0.01N |
| Superior | 1 | −0.28N | 2 | 0.34N |
| Area of | 2 | −16.67N | 3 | −15.77N |
| Curvature | 3 | −0.06N | 4 | 0.64N |
| | 4 | 29.69N | 5 | 31.03N |
| | 5 | −0.72N | 6 | −0.57N |
| | 6 | −15.54N | 7 | −15.99N |
| Inferior | 7 | 0.03N | 8 | −0.13N |
| Inferior | | | 9 | −0.01N |

For both arrangements of implanted magnetic screw devices (one vertebra superior and inferior to the area of abnormal C-type curvature, or two vertebrae superior and inferior to the area of abnormal C-type curvature), the greatest vertical force was generated at the vertebrae at the superior and inferior ends in of the area of the abnormal C-type curvature (vertebral levels 2 and 6, respectively, in FIG. 20A; vertebral levels 3 and 7, respectively, in FIG. 20B), although vertical forces were also generated in both the vertebrae immediately superior and immediately inferior to the middle vertebra in the area of the abnormal C-type curvature (vertebral levels 3 and 5, respectively, in FIG. 20A; vertebral levels 4 and 6, respectively, in FIG. 20B), and in the vertebrae superior and inferior to the area of the abnormal C-type curvature (vertebral levels 1 and 7, respectively, in FIG. 20A; vertebral levels 1, 2 and 8, 9, respectively, in FIG. 20B). A comparison of the vertical forces generated when there are magnetic screw devices implanted superior and inferior to the area of the abnormal C-type curvature to the vertical forces generated when magnetic screw devices are implanted only in the area of the abnormal C-type curvature (see Example 2) reveals that there is a large decrease in the vertical forces generated in vertebrae at the superior and inferior ends of the area of the abnormal C-type curvature when additional magnetic screw devices are implanted outside of the area of the abnormal C-type curvature (see Table 6).

TABLE 6

Vertical forces on each vertebra generated by magnetic screw devices implanted in both pedicles of adjacent vertebrae in a 5-level, 7-level, and 9-level abnormal C-type curve.

| | Level | | | | | |
|---|---|---|---|---|---|---|
| | Arrangement of Example 2 5 Adjacent Vertebrae | | Arrangement (1) of Present Example 5 7 Adjacent Vertebrae | | Arrangement (2) of Present Example 5 9 Adjacent Vertebrae | |
| | Level # | Vertical Force | Level # | Vertical Force | Level # | Vertical Force |
| Superior | | | | | 1 | −0.13N |
| Superior | | | 1 | −5.69N | 2 | −6.00N |
| Area of | 1 | −31.16N | 2 | −8.13N | 3 | −8.22N |
| Curvature | 2 | −3.50N | 3 | −4.66N | 4 | −2.08N |
| | 3 | −0.06N | 4 | 0.77N | 5 | 0.35N |
| | 4 | 3.48N | 5 | 3.70N | 6 | 3.35N |
| | 5 | 31.01N | 6 | 8.29N | 7 | 8.38N |
| Inferior | | | 7 | 5.91N | 8 | 5.93N |
| Inferior | | | | | 9 | 0.13N |

Example 6

This study analyzed the centering forces generated by implanting additional magnetic screw devices into both pedicles of vertebrae superior and inferior to the area of an abnormal S-type spinal curvature. The study considered implantation of magnetic screw devices in the following two arrangements: (1) implantation into seven adjacent vertebrae—five vertebrae in the area of an abnormal S-type curvature, one vertebra superior to the abnormal S-type curvature, and one vertebra inferior to the abnormal S-type curvature (see FIG. 23A); and (2) implantation into nine adjacent vertebrae—five vertebrae in the area of an abnormal S-type curvature, two vertebrae superior to the abnormal S-type curvature, and two vertebrae inferior to the abnormal S-type curvature (see FIG. 23B).

Under the analysis, the magnetic screw devices in the area of the abnormal S-type curvature (vertebral levels 2 to 6 in FIG. 23A; vertebral levels 3 to 7 in FIG. 23B) comprised a 2 cm×2 cm×2 cm magnet, and the magnetic screw devices immediately superior and immediately inferior to the area of the abnormal S-type curvature (vertebral levels 1 and 7 in FIG. 23A; vertebral levels 2 and 8 in FIG. 23B) comprised a 1 cm×1 cm×1 cm magnet (which has 12.5% of the magnetic strength of the 2 cm×2 cm×2 cm magnet). For arrangement (2) in which two magnetic screw devices are implanted both superior and inferior to the area of the abnormal S-type curvature, the magnetic screw devices at the superior and inferior ends (vertebral levels 1 and 9 in FIG. 23B) comprised a 0.5 cm×0.5 cm×0.5 cm magnet (which has 12.5% of the magnetic strength of the 1 cm×1 cm×1 cm magnet; and 1.6% of the magnetic strength of the 2 cm×2 cm×2 cm magnet). The offset distance between the vertebrae in the area of the abnormal curvature was 20 mm (27°). The magnetic screw devices superior to the area of the abnormal S-type curvature (vertebral level 1 in FIG. 23A; vertebral levels 1 and 2 in FIG. 23B) were aligned with the superior-most magnetic screw device in the area of the abnormal S-type curvature (vertebral level 2 in FIG. 23A; vertebral level 3 in FIG. 23B), and the magnetic screw devices inferior to the area of the abnormal S-type curvature (vertebral level 7 in FIG. 23A; vertebral levels 8 and 9 in FIG. 23B) were aligned with the inferior-most magnetic screw device in the area of the abnormal S-type curvature (vertebral level 6 in FIG. 23A; vertebral level 7 in FIG. 23B).

The results are shown in FIGS. 24 and 25 and in Table 7. For both arrangements of implanted magnetic screw devices (one vertebra superior and inferior to the area of abnormal S-type curvature, or two vertebrae superior and inferior to the area of abnormal S-type curvature), the greatest centering force was generated at the vertebrae immediately superior and immediately inferior to the middle vertebra in the area of the abnormal S-type curvature (vertebral levels 3 and 5, respectively, in FIG. 23A; vertebral levels 4 and 6, respectively, in FIG. 23B), but centering forces were also generated in vertebrae at the superior end and the inferior end of the area of the abnormal S-type curvature (vertebral levels 2 and 6, respectively, in FIG. 23A; vertebral levels 3 and 7, respectively, in FIG. 23B). The centering forces at the vertebrae immediately superior and immediately inferior to the middle vertebra in the area of the abnormal S-type curvature were each over twice in magnitude as compared to the centering forces at the vertebrae at the superior end and the inferior end of the area of the abnormal S-type curvature (see FIGS. 24 and 25, and Table 7).

This pattern is similar to the centering forces that resulted in the study described in Example 3, in which magnetic screw devices were implanted in five adjacent vertebrae in the area of an abnormal S-type spinal curvature. A comparison between the results of Example 3 and the results of the present Example 6 shows that the centering forces on the vertebrae immediately superior and immediately inferior to the middle of the abnormal S-type curvature (vertebral levels 2 and 4 in FIG. 13B of Example 3; vertebral levels 3 and 5 in FIG. 23A and vertebral levels 4 and 6 in FIG. 23B of the present Example 6) and the centering forces on the vertebrae at the ends of the area of the abnormal S-type curvature (vertebral levels 1 and 5 in FIG. 13B of Example 3; vertebral levels 2 and 6 in FIG. 23A and vertebral levels 3 and 7 in FIG. 23B of the present Example 6) were greater in the present Example 6, which suggests that the presence of the small magnets superior and inferior to the area of the abnormal S-type curvature elevates the magnitude of the centering forces experienced by the magnetic screw devices in the area of the abnormal S-type curvature.

TABLE 7

Centering forces generated by magnetic screw devices implanted in both pedicles of adjacent vertebrae in 7-level and 9-level abnormal S-type curvature.

| | Arrangement (1) 7 Adjacent Vertebrae | | Arrangement (2) 9 Adjacent Vertebrae | |
|---|---|---|---|---|
| Level | Level # | Centering Force | Level # | Centering Force |
| Superior | | | 1 | −0.01N |
| Superior | 1 | −0.14N | 2 | −0.42N |
| Area of | 2 | 14.41N | 3 | 14.23N |
| Curvature | 3 | −31.21N | 4 | −29.72N |
| | 4 | −0.45N | 5 | 0.06N |
| | 5 | 29.81N | 6 | 30.24N |
| | 6 | −13.29N | 7 | −14.70N |
| Inferior | 7 | 0.06N | 8 | −0.16N |
| Inferior | | | 9 | −0.01N |

Example 7

This study the centering forces generated by implanting additional magnetic screw devices into both pedicles of vertebrae superior and inferior to the area of an abnormal double S-type spinal curvature. The study considered implantation of magnetic screw devices in the following two arrangements: (1) implantation into seven adjacent vertebrae—five vertebrae in the area of an abnormal double S-type curvature, one vertebra superior to the abnormal double S-type curvature, and one vertebra inferior to the abnormal double S-type curvature (see FIG. 26A); and (2) implantation into nine adjacent vertebrae—five vertebrae in the area of an abnormal double S-type curvature, two vertebrae superior to the abnormal double S-type curvature, and two vertebrae inferior to the abnormal double S-type curvature (see FIG. 26B).

Under the analysis, the magnetic screw devices in the area of the abnormal double S-type curvature (vertebral levels 2 to 6 in FIG. 26A; vertebral levels 3 to 7 in FIG. 26B) comprised a 2 cm×2 cm×2 cm magnet, and the magnetic screw devices immediately superior and immediately inferior to the area of the abnormal double S-type curvature (vertebral levels 1 and 7 in FIG. 26A; vertebral levels 2 and 8 in FIG. 26B) comprised a 1 cm×1 cm×1 cm magnet (which has 12.5% of the magnetic strength of the 2 cm×2 cm×2 cm magnet). For arrangement (2) in which two magnetic screw devices are implanted both superior and inferior to the area of the abnormal double S-type curvature, the magnetic screw devices at the superior and inferior ends (vertebral levels 1 and 9 in FIG. 26B) comprised a 0.5 cm×0.5 cm×0.5 cm magnet (which has 12.5% of the magnetic strength of the 1 cm×1 cm×1 cm magnet; and 1.6% of the magnetic strength of the 2 cm×2 cm×2 cm magnet). The offset distance between the vertebrae in the area of the abnormal curvature was 20 mm (27°). The magnetic screw devices superior to the area of the abnormal double S-type curvature (vertebral level 1 in FIG. 26A; vertebral levels 1 and 2 in FIG. 26B) were aligned with the superior-most magnetic screw device in the area of the abnormal double S-type curvature (vertebral level 2 in FIG. 26A; vertebral level 3 in FIG. 26B), and the magnetic screw devices inferior to the area of the abnormal double S-type curvature (vertebral level 7 in FIG. 26A; vertebral levels 8 and 9 in FIG. 26B) were aligned with the inferior-most magnetic screw device in the area of the abnormal double S-type curvature (vertebral level 6 in FIG. 26A; vertebral level 7 in FIG. 26B).

The results are shown in FIGS. 27 and 28 and in Table 8. For both arrangements of implanted magnetic screw devices (one vertebra superior and inferior to the area of abnormal double S-type curvature, or two vertebrae superior and inferior to the area of abnormal double S-type curvature), the greatest centering force was generated at the vertebra in the middle of the area of the abnormal double S-type curvature and the vertebrae immediately superior and immediately inferior to the middle vertebra of the abnormal double S-type curvature (vertebral levels 4, 3, and 5, respectively, in FIG. 26A; vertebral levels 5, 4, and 6, respectively, in FIG. 26B), but centering forces were also generated in vertebrae at the superior end and the inferior end of the area of the abnormal double S-type curvature (vertebral levels 2 and 6, respectively, in FIG. 26A; vertebral levels 3 and 7, respectively, in FIG. 26B). The centering forces at the middle vertebra and the vertebrae immediately superior and immediately inferior to the middle vertebra in the area of the abnormal double S-type curvature were each about double in magnitude as compared to the centering forces at the vertebrae at the superior end and the inferior end of the area of the abnormal double S-type curvature (see FIGS. 27 and 28, and Table 8).

This pattern is similar to the centering forces that resulted in the study described in Example 4, in which magnetic screw devices were implanted in five adjacent vertebrae in the area of an abnormal double S-type spinal curvature. A comparison between the results of Example 3 and the results of the present Example 7 shows that the centering forces on the middle vertebra and on the vertebrae immediately superior and immediately inferior to the middle vertebra in the area of the abnormal double S-type curvature (vertebral levels 3, 2, and 4 in FIG. 17B of Example 4; vertebral levels 4, 3, and 5 in FIG. 26A and vertebral levels 5, 4, and 6 in FIG. 26B of the present Example 7) and the centering forces on the vertebrae at the ends of the area of the abnormal double S-type curvature (vertebral levels 1 and 5 in FIG. 17B of Example 4; vertebral levels 2 and 6 in FIG. 26A and vertebral levels 3 and 7 in FIG. 26B of the present Example 7) were greater in the present Example 7, which suggests that the presence of the small magnets superior and inferior to the area of the abnormal double S-type curvature elevates the magnitude of the centering forces experienced by the magnetic screw devices in the area of the abnormal double S-type curvature.

TABLE 8

Centering forces generated by magnetic screw devices implanted in both pedicles of adjacent vertebrae in 7-level abnormal double S-type curvature.

| | Arrangement (1) 7 Adjacent Vertebrae | | Arrangement (2) 9 Adjacent Vertebrae | |
|---|---|---|---|---|
| Level | Level # | Centering Force | Level # | Centering Force |
| Superior | | | 1 | −0.01N |
| Superior | 1 | 0.23N | 2 | 0.21N |
| Area of | 2 | −14.88N | 3 | −14.73N |
| Curvature | 3 | 30.31N | 4 | 29.91N |
| | 4 | −29.09N | 5 | −29.94N |
| | 5 | 30.18N | 6 | 29.88N |
| | 6 | −14.54N | 7 | −15.30N |
| Inferior | 7 | −0.18N | 8 | −0.05N |
| Inferior | | | 9 | 0.01N |

Example 8

This study analyzed how centering forces and vertical forces may be impacted by the size of magnets implanted into both pedicles of vertebrae superior and inferior to the area of an abnormal C-type spinal curvature. The study considered implantation of magnetic screw devices into seven adjacent vertebrae—five vertebrae in the area of an abnormal C-type curvature, one vertebra superior to the abnormal C-type curvature, and one vertebra inferior to the abnormal C-type curvature (see FIG. 20A).

Under the analysis, the magnetic screw devices in the area of the abnormal C-type curvature (vertebral levels 2 to 6 in FIG. 20A) comprised a 2 cm×2 cm×2 cm magnet, and the magnetic screw devices immediately superior and immediately inferior to the area of the abnormal C-type curvature (vertebral levels 1 and 7 in FIG. 20A) each comprised a 2 cm×2 cm×2 cm magnet, a 1 cm×1 cm×1 cm magnet (which has 12.5% of the magnetic strength of the 2 cm×2 cm×2 cm magnet), or a 0.5 cm×0.5 cm×0.5 cm magnet (which has 12.5% of the magnetic strength of the 1 cm×1 cm×1 cm magnet; and 1.6% of the magnetic strength of the 2 cm×2 cm×2 cm magnet). The offset distance between the vertebrae in the area of the abnormal curvature was 20 mm (27°). The magnetic screw devices superior to the area of the abnormal C-type curvature (vertebral level 1 in FIG. 20A) were aligned with the superior-most magnetic screw device in the area of the abnormal C-type curvature (vertebral level 2 in FIG. 20A), and the magnetic screw devices inferior to the area of the abnormal C-type curvature (vertebral level 7 in FIG. 20A) were aligned with the inferior-most magnetic screw device in the area of the abnormal C-type curvature (vertebral level 6 in FIG. 20A).

The results of the analysis are shown in Tables 9 and 10. Regardless of the size of the magnet superior and inferior to the area of the abnormal C-type curvature, the greatest centering force was generated at the vertebra in the middle of the area of the abnormal C-type curvature (vertebral level 4 in FIG. 20A), as well as in vertebrae at the superior end and the inferior end of the area of the abnormal C-type curvature (vertebral levels 2 and 6, respectively). The centering force at the middle vertebra of the area of the abnormal C-type curvature was still nearly twice in magnitude as compared to the centering forces at the vertebrae at the superior end and the inferior end of the area of the abnormal C-type curvature (see Table 5). Importantly, the magnitude of the centering forces at the vertebra in the middle of the area of the abnormal C-type curvature (vertebral level 4 in FIG. 20A) and at the superior end and the inferior end of the area of the abnormal C-type curvature (vertebral levels 2 and 6, respectively) was approximately the same despite the difference in size of the magnets in the vertebrae superior and inferior to the area of the abnormal C-type curvature.

TABLE 9

Centering forces generated by magnetic screw devices implanted in both pedicles of adjacent vertebrae in 7-level C-type curvature, across different sizes of magnets implanted into to the vertebrae superior and inferior to the area of the abnormal curvature.

| | | Centering Force | | |
|---|---|---|---|---|
| Level | Level # | Magnet Size: 2 cm × 2 cm × 2 cm | Magnet Size: 1 cm × 1 cm × 1 cm | Magnet Size: 0.5 cm × 0.5 cm × 0.5 cm |
| Superior | 1 | −1.01N | −0.28N | −0.01N |
| Area of | 2 | −15.89N | −16.67N | −15.72N |
| Curvature | 3 | 0.65N | −0.06N | 0.79N |
| | 4 | 31.49N | 29.69N | 30.56N |
| | 5 | −0.25N | −0.72N | −0.45N |
| | 6 | −15.29N | −15.54N | −16.13N |
| Inferior | 7 | −1.22N | 0.03N | −0.02N |

The vertical forces generated in the vertebrae differed depending on the size of the magnets implanted into the vertebrae superior and inferior to the area of the abnormal C-type curvature. When the magnet implanted into the vertebrae superior and inferior to the area of the abnormal C-type curvature was 2 cm×2 cm×2 cm, the greatest vertical force was generated in the vertebrae superior and inferior to the area of the abnormal C-type curvature, although a vertical force was also generated in the vertebrae at the superior and inferior ends in of the area of the abnormal C-type curvature. When the magnet implanted into the vertebrae superior and inferior to the area of the abnormal C-type curvature was 1 cm×1 cm×1 cm, vertical forces were generated in the vertebrae superior and inferior to the area of the abnormal C-type curvature, and in the vertebrae at the superior and inferior ends in of the area of the abnormal C-type curvature, but in each case the magnitude of the vertical force was a fraction of the vertical force generated when the magnet implanted into the vertebrae superior and inferior to the area of the abnormal C-type curvature was 2 cm×2 cm×2 cm. When the magnet implanted into the vertebrae superior and inferior to the area of the abnormal C-type curvature was 0.5 cm×0.5 cm×0.5 cm, essentially no vertical force was generated in the vertebrae superior and inferior to the area of the abnormal C-type curvature, and the vertical force generated in the vertebrae at the superior and inferior ends in of the area of the abnormal C-type curvature was only a fraction of the vertical force generated at those vertebrae when the magnet implanted into the vertebrae superior and inferior to the area of the abnormal C-type curvature was 2 cm×2 cm×2 cm. Overall, less vertical force was generated when the magnet implanted into the vertebrae superior and inferior to the area of the abnormal C-type curvature was smaller.

TABLE 10

Vertical forces generated by magnetic screw devices implanted in both pedicles of adjacent vertebrae in 7-level C-type curvature, across different sizes of magnets implanted into to the vertebrae superior and inferior to the area of the abnormal curvature.

| | | Vertical Force | | |
|---|---|---|---|---|
| Level | Level # | Magnet Size: 2 cm × 2 cm × 2 cm | Magnet Size: 1 cm × 1 cm × 1 cm | Magnet Size: 0.5 cm × 0.5 cm × 0.5 cm |
| Superior | 1 | −44.12N | −5.69N | −0.58N |
| Area of | 2 | 26.01N | −8.13N | −13.19N |
| Curvature | 3 | −1.74N | −4.66N | −2.29N |
| | 4 | 1.13N | 0.77N | −0.94N |
| | 5 | 1.40N | 3.70N | 3.69N |
| | 6 | −25.65N | 8.29N | 14.02N |
| Inferior | 7 | 41.76N | 5.91N | 0.61N |

The foregoing description is given for clearness of understanding only, and no unnecessary limitations should be understood therefrom, as modifications within the scope of the invention may be apparent to those having ordinary skill in the art.

Detailed embodiments of the present methods and magnetic devices are disclosed herein; however, it is to be understood that the disclosed embodiments are merely illustrative and that the methods and magnetic devices may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of treating a spine with an abnormal curvature in a subject in need thereof, the method comprising (a) implanting one or more magnetic screw devices into two or more vertebrae at the curvature, and (b) orienting the magnetic screw devices to align their magnetic poles, therefore treating the spine with the abnormal curvature;

wherein each magnetic screw device comprises a bone screw and one or more magnets attached thereto, wherein the bone screw comprises a stem and a housing assembly, the stem comprising a connector and at least one thread, wherein the connector of the stem is configured to articulate with the housing assembly such that the stem can rotate and angulate relative to the housing assembly;

wherein the housing assembly further comprises a locking mechanism configured to lock the housing assembly at a set rotation and angulation relative to the stem; and wherein the one or more magnets are attached to the housing assembly of the bone screw, and are not between the locking mechanism and the connector.

2. The method of claim 1, comprising implanting the one or more magnetic screw devices into one of the pedicles of each of the two or more vertebrae at the curvature.

3. The method of claim 1, comprising implanting the one or more magnetic screw devices into both pedicles of each of the two or more vertebrae at the curvature.

4. The method of claim 1, further comprising implanting one or more magnetic screw devices into two or more vertebrae that are adjacent to the vertebrae at the curvature.

5. The method of claim 1, wherein orienting the magnetic screw devices in (b) comprises orienting the housing assembly of each magnetic screw device.

6. The method of claim 5, wherein orienting the magnetic screw devices in (b) further comprises manually orienting the housing assembly of each magnetic screw device.

7. The method of claim 1, wherein the housing assembly comprises an outer shell and an inner shell, and the inner shell is fit within the outer shell.

8. The method of claim 7, wherein the inner shell comprises a hollow cylinder.

9. The method of claim 8, wherein the connector of the stem is configured to articulate with the inner shell of the housing assembly.

10. The method of claim 9, wherein the connector is generally spherical or partially spherical.

11. The method of claim 10, wherein the inner surface of the inner shell comprises concave or partially concave curvatures.

12. The method of claim 7, wherein the outer shell comprises a general shape of a hollow cylinder that comprises an upper section with an upper end, a lower section with a lower end, and an outer surface and an inner surface; and wherein the one or more magnets are attached to the upper end of the outer shell of the housing assembly.

13. The method of claim 1, wherein the locking mechanism comprises a set screw.

14. The method of claim 1, further comprising locking the locking mechanism after orienting the magnetic screw devices.

15. The method of claim 1, wherein the one or more magnets are attached to the locking mechanism.

16. The method of claim 1, wherein the one or more magnets are enclosed in a casing.

17. The method of claim 1, wherein the one or more magnets comprise a material that is iron-based, nickel-based, cobalt-based, or an alloy of rare-earth metals.

18. The method of claim 17, wherein the one or more magnets comprise an alloy of neodymium, iron, and boron.

19. The method of claim 1, wherein the abnormal curvature is selected from an abnormal C-type curvature, an abnormal S-type curvature, and an abnormal double S-type curvature.

* * * * *